(12) United States Patent
Schreiber et al.

(10) Patent No.: US 6,982,082 B1
(45) Date of Patent: Jan. 3, 2006

(54) GENE THERAPY BY CELL SPECIFIC TARGETING

(75) Inventors: Stuart L. Schreiber, Boston, MA (US); Peter J. Belshaw, Somerville, MA (US); Gerald Crabtree, Woodside, CA (US)

(73) Assignees: President and Fellows of Harvard College, Cambridge, MA (US); Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 08/922,240

(22) Filed: Aug. 27, 1997

Related U.S. Application Data

(60) Provisional application No. 60/024,484, filed on Aug. 27, 1996.

(51) Int. Cl.
*A61K 48/00* (2006.01)
*C12N 5/00* (2006.01)
*C12N 15/00* (2006.01)
*C12N 15/63* (2006.01)
*C12N 15/74* (2006.01)

(52) U.S. Cl. .................. 424/93.21; 424/93.2; 424/93.1; 514/44; 435/69.1; 435/320.1; 435/325; 435/335; 435/355; 435/372

(58) Field of Classification Search .................. 514/44; 424/93.1, 93.21, 93.2; 435/375, 325, 320.1, 435/343, 355, 372, 69.1, 6, 370.1, 335; 536/23.5
See application file for complete search history.

(56) References Cited

FOREIGN PATENT DOCUMENTS

| WO | WO 94/18317 | 8/1994 |
|---|---|---|
| WO | WO 95/02684 | 1/1995 |
| WO | WO 96 06097 | 2/1996 |
| WO | WO 96 12806 | 5/1996 |

OTHER PUBLICATIONS

Bron, D. (1994) Curr. Opin. Oncol., vol. 6, 358-364.*
Hertenstein et al. (Feb. 1998) BioDrugs, vol. 9 (2), 105-123.*
Blazer et al. (1997) Immunological Reviews, vol. 157, 79-109.*
Deonarin et al. (Jan. 1998) Exp. Opin. Ther. Patents, vol. 8 (1), 53-69.*
Miller et al. (1995) FASEB, vol. 9, 190-199.*
Mori et al. (1997) J. Immunol., vol. 158, 3659-3665.*
Fruman et al. Molecular and Cellular Biology 15:3857-3863, 1995.*
Kawamura et al. The Journal of Biological Chemistry 270: 15463-15466, 1995.*
Futer O., "FK506 Binding Protein Mutational Analysis", 270/32 J. Biol. Chem., 18935-18940 (1995).
DeCenzo, M.T., "FK506-binding Protein Mutational Analysis: Defining the Active Site Residue Contributions to Catalysis and the Stability of Ligand Complexes", 9/2 Protein Engineering, 173-180, (1996).
Luengo J.I., "Structure-Activity Studies of Rapamycin Analogs: Evidence that the C-7 Methoxy Group is Part of the Effector Domain and Positioned at the FKBP 12-FRAP Interface", 2/7 Chemistry and Biology 471-481 (1995).
Brown et al. "A signalling pathway to translational control" Cell, 86:517 (1996).
Hung et al. "Understanding and controlling the cell cycle with natural products" Chemistry & Biology 3: 623 (1996).
Belshaw et al. "Rational design of orthogonal receptor-ligand combinations" Angew. Chem. Int. Ed. Engl. 34:2129 (1995).
Rosen et al. "Natural products as probes of cellular function: studies of immunophilins" Angew. Chem. Int. Ed. Engl. 31: 384 (1992).
International Search Report mailed Apr. 29, 1998.

* cited by examiner

*Primary Examiner*—Anne M. Wehbé
(74) *Attorney, Agent, or Firm*—Fish & Neave IP Group of Ropes & Gray, LLP

(57) ABSTRACT

This invention is directed to a modified cyclosporin A and to a modified, genetically engineered version of its receptor, cyclophilin. This invention is further directed to a method for treating host versus graft disease following blood marrow transplantation by transfecting stem cells so that after introduction into a patient the stem cells will express the modified cyclophilin, and, as necessary, administer the modified cyclosporin A to the patient.

11 Claims, 4 Drawing Sheets

GENE THERAPY BY CELL SPECIFIC TARGETING

This application claims the benefit of provisional application 60/024,484 filed Aug. 27, 1996.

STATEMENT OF RIGHTS

This invention was partially funded by NIH Grant No. GM-38627. Therefore the Government has certain rights in the invention.

BACKGROUND OF THE INVENTION

Tolerance to self major histocompatibility (MHC) antigens occurs during T cell maturation in the thymus. During ontogeny, exposure of the immune system to MHC antigens results in the loss of reactivity to those antigens, thus leaving the animal specifically tolerant into adult life. Inducing tolerance in adult animals has been accomplished by high-dose cytoreductive therapy and bone marrow transplantation.

Bone marrow transplantation has been found to be effective in the control of certain malignant lymphohematopoietic diseases where conventional chemotherapy has failed or would be expected to fail. There are attendant disadvantages to bone marrow transplantation. Often there is an allogeneic antitumor effect independent of the chemoradiotherapy of the preparative regimen. This adoptive immunotherapy effect is, in large measure, accompanied by graft-versus-host (GVH) disease.

Historically, GVH disease has been a major cause of serious morbidity and death after bone marrow transplantation. Graft-versus-host disease and its treatment are accompanied by profound immunodeficiency and immune dysregulation, which places the patient at risk for life-threatening infections and other complications. GVH disease has accounted for approximately two thirds of the deaths after allogeneic bone marrow transplantation.

Removing T lymphocytes in allogeneic bone marrow inocula to prevent GVH disease is associated with increased rates of engraftment failure. While these drawbacks are generally considered acceptable for the treatment of otherwise lethal malignant diseases, they would severely limit the application of MHC mismatched bone marrow transplantation as a preparative regimen for organ transplantation, in which nonspecific immunosuppressive agents, while not without major complications, are effective.

Since GVH disease is immunologically mediated, efforts to prevent its development have involved the use of immunosuppressive therapy. Of the many agents studied, methotrexate, glucocorticoids, and cyclosporin have been found to be useful. It is a continuing goal to develop better treatments for patients in need of a bone marrow transplant or other diseases that can be specifically cell targeted.

SUMMARY OF THE INVENTION

One embodiment of the present invention provides a method for selectively inhibiting proliferation of a hematopoietic cell by contacting a cell which ectopically expresses a mutated macrolide binding protein (MBP) with a macrolide which selectively induces macrolide-dependent inhibition of proliferation of cells expressing the mutated MBP compared to cells expressing a wild-type form of the MBP. In such embodiments, the mutated MBP has an altered macrolide-binding specificity relative to the wild-type form MBP, e.g., which provides the specificity for macrolide-dependent inhibition.

In another embodiment, the invention provides a method for selectively inhibiting proliferation of a hematopoietic cell comprising: (i) causing, in the cell, the ectopic expression of an MBP gene encoding a mutated macrolide binding protein (MBP) having an altered macrolide-binding specificity relative to a wild-type form of the MBP, which mutated MBP retains the ability to cause macrolide-dependent inhibition of proliferation; and (ii) contacting the cell with a macrolide which selectively binds to the altered MBP relative to the wild-type MBP and selectively induces macrolide-dependent inhibition of proliferation of cells expressing the mutated MBP relative to cells not expressing only the wild-type MBP.

In yet another embodiment, there is provided a method for selectively inhibiting proliferation of a transplanted hematopoietic cell by the steps of (i) transplanting, into an animal, hematopoietic cells which ectopically expresses a MBP gene encoding a mutated macrolide binding protein (MBP), the mutated MBP having an altered macrolide-binding specificity relative to the wild-type form MBP; and (ii) administering to the animal an amount of a macrolide sufficient to inhibit proliferation of the transplanted cells, which macrolide selectively induces macrolide-dependent inhibition of proliferation of cells expressing the mutated MBP compared to cells expressing a wild-type form of the MBP.

In still another embodiment, the there is provides a method for treating graft-versus-host disease in an animal by selectively inhibiting proliferation of hematopoietic cells contained a transplanted tissue. Such methods are particularly useful in the transplantation of bone marrow or hematopoeitic stem cells. The method generally comprises transducing, e.g., before implantation, at least a sub-population of hematopoietic cells of the transplanted tissue with a gene for ectopic expression of a mutated macrolide binding protein (MBP), the mutated MBP having an altered macrolide-binding specificity relative to the wild-type form MBP. Prior to, concurrent with and/or subsequent to transplanting the tissue, the animal (or cells in culture) are treate with an amount of a macrolide sufficient to inhibit proliferation of the hematopoeitic transplanted cells, which macrolide selectively induces macrolide-dependent inhibition of proliferation of the transplanted cells expressing the mutated MBP compared to endogenous cells of the animal.

In another embodiment, the invention provides a method for promoting engraftment and hematopoietic activity of a hematopoietic stem cell, comprising: (a) transducing the stem cells to be engrafted with a nucleic acid encoding a modified macrolide binding protein specific for a modified macrolide, e.g., to produce a transformed hematopoietic stem cell; (b) introducing the transformed hematopoietic stem cell into a recipient mammal, such that the modified cellular receptor cyclophilin is expressed; and (c) administering to the animal an effective amount of the modified cyclosporin.

In the subject methods described herein, such as those enumerated above, the MBP can be a FRAP, an FK506-binding protein, a cyclophilin or a calcineurin. Preferably, the mutated MBP has a dissociation constant, $K_d$, for a modified macrolide which is at least one order of magnitude less than the $K_d$ of the wild-type MBP, though mutated MBP with dissociation constants at least two, three, four, five and even ten orders of magnitude less than the $K_d$ of the wild-type MBP are contemplated.

The mutated MBP gene can be provided in a cell as part of an expression vector, such as a viral expression construct. In certain embodiments, the mutated MBP gene is introduced into the genome of the cell by homologous recombination or other integration techniques.

In preferred embodiments, the macrolide is an analog of rapamycin, FK506 or cyclosporin.

Preferred cells for use in the subject methods are mammalian cells, more preferably primate cells, and even more preferably human cells.

Preferred animals for treatemtn by the subject methods are mammals, more preferably primates, and even more preferably humans.

In those instances where the engineered cells are transplanted into an animal, the cells are preferably from an autologous source.

For treatment, the subject method can be used where the treated animal is in an immunosuppressed state, e.g., as a result of radiation or chemotherapy.

Another aspect of the present invention provides expression constructs encoding a mutated macrolide binding protein (MBP) selected from the group consisting of FRAP, FKBP, cyclophilin and calcineurin, wherein the mutated MBP has an altered macrolide-binding specificity relative to the wild-type form MBP and, in the presence of a macrolide which binds the mutated MBP, induces macrolide-dependent inhibition of proliferation of a cell expressing the mutated MBP.

The present invention also provides hematopoeitic cells, particularly stem cells and/or T cells, which have been engineered with such expression constructs.

Yet another aspect of the present invention relates to kits for for selectively inhibiting proliferation of a hematopoietic cell. The subject kits can include (i) an expression construct for ectopically expressing an MBP gene encoding a mutated macrolide binding protein (MBP) having an altered macrolide-binding specificity relative to a wild-type form of the MBP, which mutated MBP retains the ability to cause macrolide-dependent inhibition of proliferation; and (ii) a macrolide which selectively binds to the altered MBP relative to the wild-type MBP and selectively induces macrolide-dependent inhibition of proliferation of cells expressing the mutated MBP relative to cells not expressing only the wild-type MBP.

DETAILED DESCRIPTION OF THE INVENTION

I. General

Figure 1:
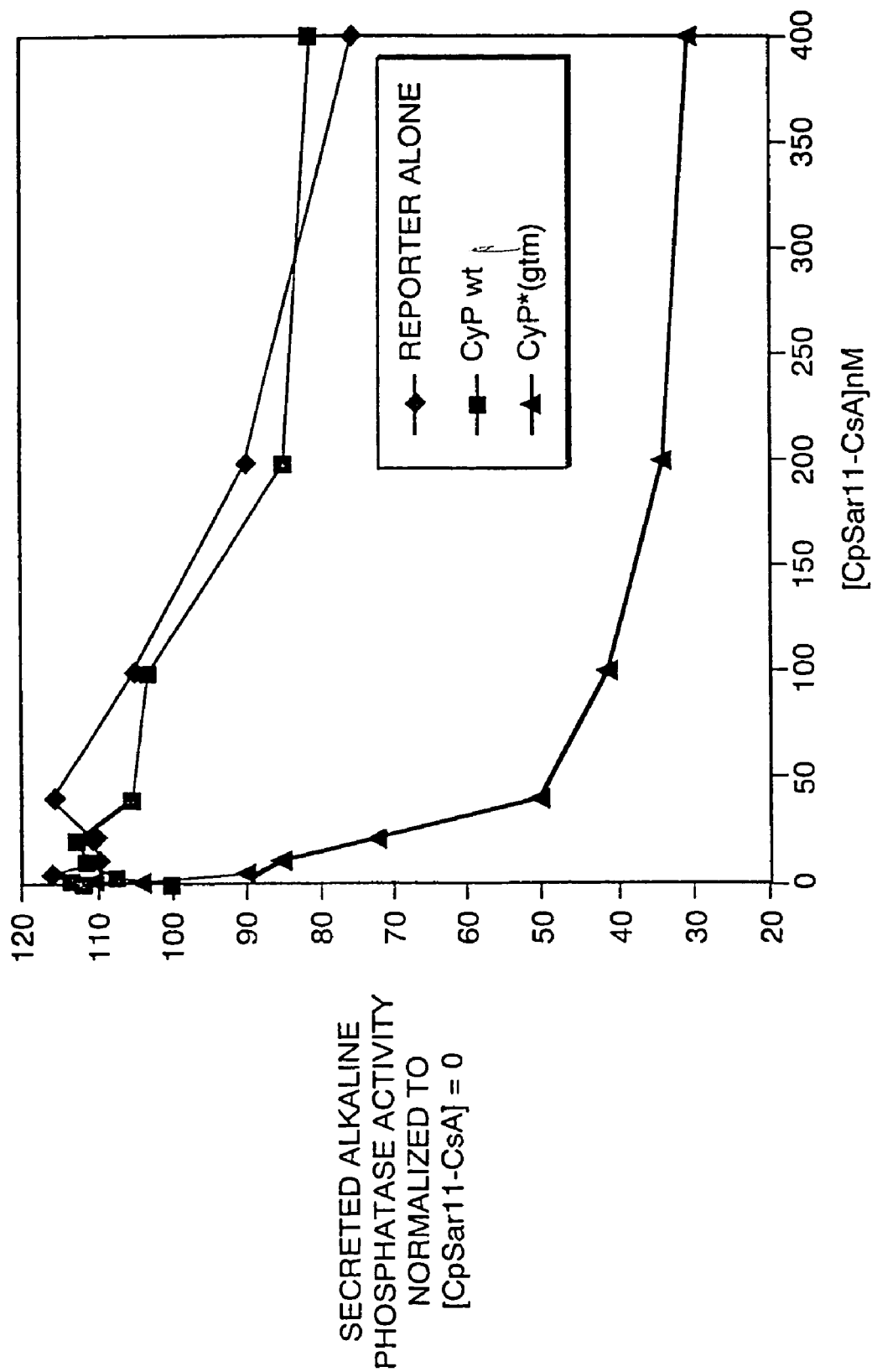
FIG. 1 is a graph showing the cellular assay for calcineurin-mediated NFAT-signalling.

The invention pertains to methods for regulating a biological activity of a cell, preferably in a tissue-type or cell-type specific manner. In general, the present invention provides a method for rendering a cell selectively sensitive to a macrolide analog. The present invention is based, inter alia, on the observation that, by compensatory mutation, macrolide-dependent protein—protein interactions, e.g., mediated by macrolides, can be recapitulated in systems where the macrolide has been altered (as a "modified ligand") to no longer interact efficiently with a ligand-binding domain (LBD) of one of the proteins ("target protein") found in macrolide-dependent complexes. In particular, compensatory mutations can be made to the ligand binding domain of a target protein which is not otherwise able to efficiently bind to the modified ligand, and in doing so render the modified target protein able to bind to the modified ligand.

According to the invention, a biological activity of a cell which is contingent on the presence or absence of macrolide-dependent protein complexes can be regulated by treatment with the modified ligand and concomitant expression of a target protein engineered to bind to the modified form of the ligand. Upon expression of the genetically engineered target protein, the modified ligand can selectively bind to or otherwise interact with the engineered protein so as to recruit and/or stabilize the formation of a macrolide-dependent protein complex. In preferred embodiments, the modified ligand will not similarly interact with or induce formation of similar complexes in wild-type cells. Thus, the invention provides the ability to selectively regulate biological events mediated by the protein target. Treatment of wild-type cells (i.e., cells which do not express the modified protein) with the modified ligand will have essentially no impact on the biological activity in those cells, whereas treatment of cells expressing the modified protein with the modified ligand will induce the biological activity.

To provide further guidance, the following three examples illustrate certain aspects of the invention:

(A) The macrolide rapamycin mediates the formation of complexes including an FK506-binding protein (FKBP), such as FKBP12 (SEQ ID NO. 1), and a FRAP (tor1) protein (SEQ ID No. 2). The formation of the rapamycin-dependent complexes correlates with cell-cycle arrest in G1 phase, and is understood to be part of the mechanism by which rapamycin obtains its immunosuppressive, antiproliferative and antineoplastic activities. As described below, there are a variety of rapamycin analogs which bind FRAP and/or FKBP12 with a much reduced affinity (e.g., with $K_d$ values which are orders of magnitude greater than rapamycin). By compensatory mutation to, for example, the ligand-binding domain of FRAP, formation of rapamycin-dependent FRAP/FKBP complexes by certain of those analogs can be restablished. Accordingly, a cell can be rendered sensitive to such rapamycin analogs by ectopic expression of a gene encoding a compensatory mutant of FRAP. Similarly, where the modification of rapamycin results in loss of efficient interaction with an FKBP, compensatory mutations to that protein can be used to provide FRAP/FKBP complexes dependent on the presence of the modified rapamycin.

(B) The macrolide FK506 can bring about certain biological events, like cell-cycle arrest, by a mechanism which apparently includes induction of FK506-dependent complexes of an FKBP and the calcineurin protein (SEQ ID No. 3). Various analogs of FK506 can be made which disrupt the ability of the analog to interact with one or both of the FKBP and calcineurin proteins, or at least disrupt the formation of macrolide-dependent complexes. As above, compensatory mutants can be provided which restore the ability of the analog to induce such biological responses as inhibition of proliferation.

(C) Yet another example of a macrolide-dependent system which can be usurped for use in the present invention involves the cyclosporin-dependent complexes including a cyclophilin and a calcineurin. As above, pairs of cyclosporin analogs and compensatory mutants of one or both of the cyclophilin and/or calcineurin proteins can be used to render cell populations selectively sensitive to treatment with the analog.

Thus, in a generic sense, the present invention provides a method for selectively inhibiting proliferation of a cell by (i) contacting the cell with a macrolide which does not efficiently bind to a native macrolide binding protein (MBP) of the cell, under conditions wherein (ii) the cell ectopically expresses a mutated form of the MBP which causes inhibition of proliferation in a manner dependent on the presence of the macrolide. For example, the MBP can be engineered with compensatory mutations sufficient to decrease the dissociation constant ($k_d$) for binding to macrolide, e.g., relative to the native MBP, preferably by at least 1, 2, 3 or even 5 or more orders of magnitude.

In a preferred embodiment of the invention, tissue specificity for controlling the effect of treatment with the macrolide is achieved by selective transduction of a gene encoding the modified MBP, and/or by operably linking that gene to a transcriptional regulatory sequence having the desired cell-type or tissue-type specificity for expression. In other embodiments, tissue specificity is provided by tissue-specific delivery of the macrolide.

Exemplary biological activity that can be regulated according to the method of the invention can be cellular proliferation, differentiation, and/or cell death and/or regulation of gene expression, so long as the biological activity is regulated or otherwise mediated by the ligand-crosslinked protein complex. In a preferred embodiment, the biological activity is T cell activation.

Exemplary target proteins which can be engineered in the practice of the subject invention include those intracellular proteins which form protein complexes in a macrolide-dependent fashion, and include cyclophilins, calcineurins, FK506 binding proteins (FKBPs) and FRAP (Tor1), which have mutated ligand binding domains for interacting with such macrolides as altered forms of cyclosporins, FK506 or rapamycin, e.g., which effect the formation of cyclophilin-calcineurin, FKBP-calcineurin and FKBP-FRAP complexes.

II. Definitions

For convenience, the meaning of certain terms and phrases employed in the specification, examples, and appended claims are provided below.

As used herein, the term "cellular composition" refers to a preparation of cells, which preparation may include, in addition to the cells, non-cellular components such as cell culture media, e.g. proteins, amino acids, nucleic acids, nucleotides, co-enzyme, antioxidants, metals and the like. Furthermore, the cellular composition can have components which do not affect the growth or viability of the cellular component, but which are used to provide the cells in a particular format, e.g., as polymeric matrix for encapsulation or a pharmaceutical preparation.

The term "lineage committed cell" refers to a stem cell that is no longer pluripotent but has become restricted to a specific lineage, e.g., a myeloid, lymphoid, erythroid lineage. the lineage committed cell subsequently differentiates to specialized cell types, e.g., erythrocytes, T and B lymphocytes.

The term "stem cell" refers to an undifferentiated cell which is capable of self-renewal, i.e., proliferation to give rise to more stem cells, and may give rise to lineage committed progenitors which are capable of differentiation and expansion into a specific lineage. In a preferred embodiment, the term "stem cell" refers to a generalized mother cell whose descendants (progeny) specialize, often in different directions, by differentiation, e.g., by acquiring completely individual characters, as occurs in progressive diversification of embryonic cells and tissues. As used herein, the term "stem cells" refers generally to both embryonic and hematopoietic stem cells from mammalian origin, e.g., human.

A stem cell composition is characterized by being able to be maintained in culture for extended periods of time, being capable of selection and transfer to secondary and higher order culture, and being capable of differentiating into various lymphoid or myeloid lineages, particularly B and T lymphocytes, monocytes, macrophages, neutrophils, erythrocytes and the like.

As used herein, the term "embryonic stem cell" means a pluripotent, blastocyst-derived cell that retains the developmental potential to differentiate into all somatic and germ cell lineages (for review, see Robertson, E. J. (1986) Trends in Genetics 2: 9–13). This cell type is also referred to as an "ES cell".

As used herein, the term "hematopoietic stem cell" (HSC) means a population of cells capable of both self-renewal and differentiation into all defined hematopoietic lineages, i.e., myeloid, lymphoid or erythroid lineages; and limiting number of cells are capable of repopulating the hematopoietic system of a recipient who has undergone myeloablative treatment. HSCs can ultimately differentiate into "hematopoietic cells", including without limitation, common lymphoid progenitor cells, T cells (e.g., helper, cytotoxic, and suppressor cells), B cells, plasma cells, natural killer cells, common myeloid progenitor cells, monocytes, macrophages, mast cells, leukocytes, basophils, neutrophils, eosinophils, magakaryocytes, platelets, and erythroids. HSCs are identifiable by the presence of cell surface antigens of primitive phenotypes, e.g., CD34+Thy-1$^+$Lin$^-$, and negative staining for lineage-specific antigens.

As used herein, the term "gene" or "recombinant gene" refers to a nucleic acid molecule comprising an open reading frame and including at least one exon and (optionally) an intron sequence. The term "intron" refers to a DNA sequence present in a given gene which is not translated into protein and is generally found between exons.

As used herein, the term "nucleic acid" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides.

The term "operably linked" when referring to a transcriptional regulatory sequence and a coding sequence is intended to mean that the regulatory sequence is associated with the coding sequence in such a manner as to facilitate transcription of the coding sequence in an activator-dependent fashion.

As used herein, "heterologous DNA" or "heterologous nucleic acid" include DNA that does not occur naturally as part of the genome in which it is present or which is found in a location or locations in the genome that differs from that in which it occurs in nature. Heterologous DNA is not endogenous to the cell into which it is introduced, but has been obtained from another cell. Generally, although not necessarily, such DNA encodes RNA and proteins that are not normally produced by the cell in which it is expressed.

Heterologous DNA may also be referred to as foreign DNA. Any DNA that one of skill in the art would recognize or consider as heterologous or foreign to the cell in which is expressed is herein encompassed by heterologous DNA.

"Transcriptional regulatory sequence", also termed herein "regulatory element", "regulatory sequence" or "regulatory element", are generic terms used throughout the specification to refer to DNA sequences, such as initiation signals, enhancers, and promoters, which induce or control transcription of protein coding sequences with which they are operably linked. The term "enhancer", also referred to herein as "enhancer element", is intended to include regulatory elements capable of increasing, stimulating, or enhancing transcription from a basic promoter. The term "silencer", also referred to herein as "silencer element" is intended to include regulatory elements capable of decreasing, inhibiting, or repressing transcription from a basic promoter. Regulatory elements can also be present in genes other than in 5' flanking sequences. Thus, it is possible that regulatory elements of a gene are located in introns, exons, coding regions, and 3' flanking sequences.

The terms "basic promoter" or "minimal promoter", as used herein, are intended to refer to the minimal transcriptional regulatory sequence that is capable of initiating transcription of a selected DNA sequence to which it is operably linked. This term is intended to represent a promoter element providing basal transcription. A basic promoter frequently consists of a TATA box or TATA-like box and is bound by an RNA polymerase and by numerous transcription factors, such as GTFs and TATA box Binding Proteins (TBPs).

The term "tissue specific regulatory element" refers to promoters and other regulatory elements which effect expression of an operably linked DNA sequence preferentially in specific cell-types or tissue-types. Gene expression occurs preferentially in a specific cell if expression in this cell type is significantly higher than expression in other cell types.

The terms "promoter" and "regulatory element" also encompass so-called "leaky" promoters and "regulatory elements", which regulate expression of a selected DNA primarily in one tissue, but cause expression in other tissues as well. The terms "promoter" and "regulatory element" also encompass non-tissue specific promoters and regulatory elements, i.e., promoters and regulatory elements which are active in most cell types. Furthermore, a promoter or regulatory element can be a constitutive promoter or regulatory element, i.e., a promoter or regulatory element which constitutively regulates transcription, as opposed to a promoter or regulatory element which is inducible, i.e., a promoter or regulatory element which is active primarily in response to a stimulus. A stimulus can be, e.g., a molecule, such as a hormone, a cytokine, a heavy metal, phorbol esters, cyclic AMP (cAMP), or retinoic acid.

As used herein, the terms "transfection" and "transduction" mean the introduction of a nucleic acid, e.g., an expression vector, into a recipient cell by nucleic acid-mediated gene transfer. The term "transduction" is generally used herein when the transfection with a nucleic acid is by viral delivery of the nucleic acid. "Transformation", as used herein, refers to a process in which a cell's genotype is changed as a result of the cellular uptake of exogenous DNA or RNA, and, for example, the transformed cell expresses a recombinant form of a polypeptide or, in the case of antisense expression from the transferred gene, the expression of a naturally-occurring form of the recombinant protein is disrupted.

As used herein, the term "transgene" refers to a nucleic acid sequence which has been introduced into a cell. Daughter cells deriving from a cell in which a transgene has been introduced are also said to contain the transgene (unless it has been deleted). A transgene can encode, e.g., a polypeptide, partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene). Alternatively, a transgene can also be present in an episome. A transgene can include one or more transcriptional regulatory sequences and any other nucleic acid, (e.g. intron), that may be necessary for optimal expression of a selected coding sequence.

By "gene product" it is meant a molecule that is produced as a result of transcription of a gene. Gene products include RNA molecules transcribed from a gene, as well as proteins translated from such transcripts.

The terms "protein", "polypeptide" and "peptide" are used interchangeably herein when referring to a gene product, e.g., as may be encoded by a coding sequence.

The terms "mutated" and "non-native" are used interchangeably herein and refer to genes and genes products which are not native (do not naturally occur) in the particular cell in which they are present, e.g., the term refers to a state relative to the cell's genotype. Thus, mutant (or non-native) MBPs are proteins which have altered sequences relative to the host cell, and which may have been generated by, for example, mutagenesis, or which could be MBPs found naturally in other cells.

The term "interact" as used herein is meant to include detectable interactions between molecules, such as can be detected using, for example, a yeast two hybrid assay or by immunoprecipitation. The term interact is also meant to include "binding" interactions between molecules. Interactions may be, for example, protein—protein, protein-nucleic acid, protein-small molecule or small molecule-nucleic acid in nature.

The term "ligand binding domain" (or "LBD") refers to any protein, though generally a fragment thereof or derivative thereof, which binds a preselected ligand.

The term "wild-type ligand binding domain" refers to a ligand binding domain as it is naturally occurring in a normal cell.

The term "modified ligand binding domain" refers to any ligand binding domain which has been modified, or altered to decrease binding of the naturally occurring ligand to the modified LBD. The modified LBD is preferably capable of interacting specifically with a modified ligand, which is not capable of interacting significantly with the naturally occurring ligand binding domain. A modification of a ligand may consist of the addition, deletion or substitution of at least one atom or chemical moiety of the ligand. If the ligand is a proteinous compound, the modification can be an addition, deletion, or substitution of one or more amino acids or the modification of at least one amino acid.

The term "ligand" refers to any molecule which is capable of interacting with a receptor. A ligand can be naturally occurring, or the ligand can be partially or wholly synthetic. Preferred ligands include macrolides, e.g, cyclosporin A, FK506, and rapamycin and analogs thereof.

The term "modified ligand" refers to a ligand which has been modified such that it does not significantly interact with the naturally occurring receptor of the ligand in its non modified form.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Derived from" as that phrase is used herein indicates a peptide or nucleotide sequence selected from within a given sequence. A peptide or nucleotide sequence derived from a named sequence may contain a small number of modifications relative to the parent sequence, in most cases representing deletion, replacement or insertion of less than about 15%, preferably less than about 10%, and in many cases less than about 5%, of amino acid residues or base pairs present in the parent sequence. In the case of DNAs, one DNA molecule is also considered to be derived from another if the two are capable of selectively hybridizing to one another.

As used herein, the term "animal" refers to mammals, preferably mammals such as humans. Likewise, a "patient" or "subject" to be treated by the method of the invention can mean either a human or non-human animal.

A "disease of a hematopoietic cell" refers to any condition characterized by impairment of any normal function of a hematopoietic cell. The diseases of hematopoietic cells that can be treated utilizing the cells of the present invention include, without limitation, genetic disorders (e.g., Adenosine Deaminase Deficiency, Fanconis' Anemia, and hemoglobinopathies such as Sickle Cell Anemia, Thalassemias, and Hemogobin C Disease), as well as diseases acquired by infectious or non-infectious means (e.g., Acquired Immune Deficiency Syndrome and leukemias).

A "discordant species combination", as used herein, refers to two species in which hyperacute rejection occurs when vascular organs are grafted. Generally, discordant species are from different orders, while non-discordant species are from the same order.

III. Exemplary Modified Macrolides and Macrolide-binding proteins

The modified target proteins are those forms of a protein which, relative to a naturally occuring form of the protein, have been altered at the amino acid level to increase the binding affinity of the target protein or a complex including the target protein for a modified macrolide ligand. Generally, such alterations will be made to a ligand binding domain of the target protein.

A wide range of techniques are known in the art for generating the modified target proteins of the present invention. In one embodiment, crystallographic or other structural data pertaining to the interaction of the normal ligand with the native protein can be consulted to predict compensatory mutations to the protein to restore binding to the modified ligand. In other embodiments, combinatorial mutagenisis can be used to isolate mutated forms of the target protein by their binding affinity for the modified ligand. The mutations introduced into the target protein can involve changes in amino acid residues known to be at the binding site, or by random or semi-random mutagenesis.

There are a host of methods available in the art for screening gene products of variegated gene libraries made by combinatorial mutagenesis, especially for identifying individual gene products having a certain binding property. Such techniques will be generally adaptable for rapid screening of gene libraries generated by the combinatorial mutagenesis of, for example, the macrolide binding domain of any of an FKBP, cyclophilin, calcineurin and/or FRAP protein. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate ligand binding domain sequences created by combinatorial mutagenesis techniques.

In one screening assay, the candidate ligand binding domains are displayed on the surface of a cell or viral particle, preferably in truncated form, and the ability of particular cells or viral particles to bind as appropriate, e.g., FK506, cyclosporin or rapamycin (or a protein complex thereof) via the displayed ligand binding domain is detected in a "panning assay". For instance, the degenerate LBD gene library can be cloned into the gene for a surface membrane protein of a bacterial cell, and the resulting fusion protein detected by panning protocols (see, for example, Ladner et al., WO 88/06630; Fuchs et al. (1991) *Bio/Technology* 9:1370–1371; and Goward et al. (1992) *TIBS* 18:136–140). In a similar fashion, fluorescently labeled molecules which bind the LBD, such as fluorescently labeled forms of the altered macrolide alone or in preformed protein complexes, can be used to score for ligand binding domains which are capable of interacting with the modified ligand. Cells can be visually inspected and separated under a fluorescence microscope, or, where the morphology of the cell permits, separated by a fluorescence-activated cell sorter.

In an alternate embodiment, the gene library is expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filamentous phages M13, fd, and f1 are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) *J. Biol. Chem.* 267:16007–16010; Griffiths et al. (1993) *EMBO J.* 12:725–734; Clackson et al. (1991) *Nature* 352:624–628; and Barbas et al. (1992) *PNAS* 89:4457–4461).

In an illustrative embodiment, the recombinant phage antibody system (RPAS, Pharmacia Catalog number 27-9400-01) can be easily modified for use in expressing and screening LBD combinatorial libraries. For instance, the pCANTAB 5 phagemid of the RPAS kit contains the gene which encodes the phage gIII coat protein. A combinatorial library of coding sequences for macrolide binding domains can be cloned into the phagemid adjacent to the gIII signal sequence such that it will be expressed as a gIII fusion protein. After ligation, the phagemid is used to transform competent E. coli TG1 cells. Transformed cells are subsequently infected with M13KO7 helper phage to rescue the phagemid and its candidate LBD gene insert. The resulting recombinant phage contain phagemid DNA encoding a specific candidate protein, and display one or more copies of the corresponding fusion coat protein. The phage-displayed candidate LBD which are capable of binding to the modified macrolide, or a complex thereof, are selected or enriched by panning. For instance, a phage library of mutant LBDs derived from FKBP12 can be panned on a polymer-immobilized form of the modified FK506, and unbound phage washed away from the insoluble matrix. The bound phage is then isolated, and if the recombinant phage express at least one copy of the wild type gIII coat protein, they will retain their ability to infect E. coli. Thus, successive rounds of reinfection of E. coli, and panning will greatly enrich for variant LBDs retaining the ability to bind to the modified FK506 in each round.

In light of the present disclosure, a variety of forms of mutagenesis generally applicable will be apparent to those skilled in the art, and most will be amenable to the aforementioned combinatorial mutagenesis approach. For example, modified ligand binding domains which can bind to the modified ligand can be generated and screened using, for example, alanine scanning mutagenesis and the like (Ruf et al. (1994) Biochemistry 33–1565–1572; Wang et al. (1994) J Biol Chem 269:3095–3099; Balint et al. (1993) Gene 137:109–118; Grodberg et al. (1993) Eur J Biochem 218:597–601; Nagashima et al. (1993) J Biol Chem 268: 2888–2892; Lowman et al. (1991) Biochemistry 30:10832–10838; and Cunningham et al. (1989) Science 244:1081–1085), by linker scanning mutagenesis (Gustin et al. (1993) Virology 193:653–660; Brown et al. (1992) Mol Cell Biol 12:2644–2652; McKnight et al. (1982) Science 232:316); or by saturation mutagenesis (Meyers et al. (1986) Science 232:613).

Where mutagenesis of a fragment of the full length target protein is carried out, the coding sequence for an isolated modified form of that fragment is reengineered back into the context of the full length gene, or a portion sufficient to induce the desired biological activity, such as by techniques used to generate fusion proteins.

In preferred embodiments, the modified ligand binding domain binds to the modified ligand with a dissociation constant approaching that observed for interaction of the wild-type macrolide receptor and unmodified ligand. In preferred embodiments, the target protein is modified to contain ligand-binding domains which bind to a preselected modified macrolide with a $K_d$ value below about $10^{-6}$M, more preferably below about $10^{-7}$ M, even more preferably below about $10^{-8}$M, and in some embodiments below about $10^{-9}$M. Other modified macrolide binding domains useful in the present invention, including mutants thereof, are described in the art. See, for example, WO96/41865, WO96/13613, WO96/06111, WO96/06110, WO96/06097, WO96/12796, WO95/05389, WO95/02684, WO94/18317, each of which is expressly incorporated by reference herein.

In selecting a modified ligand, e.g., a modified macrolide, for use in the subject method, there are a number of readily observable or measurable criteria which can be (optionally) considered: (A) the ligand is physiologically acceptable (i.e., lacks undue toxicity towards the cell or animal for which it is to be used), (B) it has a reasonable therapeutic dosage range, (C) desirably (for applications in whole animals), it can be taken orally (is stable in the gastrointestinal system and absorbed into the vascular system), (D) it can cross the cellular and other membranes, as necessary, and (E) binds to a modified ligand binding domain with reasonable affinity for the desired application. A first desirable criterion is that the compound is relatively physiologically inert, but for its activating capability with the modified protein complexes. The less the ligand binds to native macrolide binding proteins, and the lower the proportion of total ligand which binds to such proteins, the better the response will normally be. Particularly, the ligand should not have a strong biological effect on native proteins.

Preferred ligands include modified forms of cyclosporin A, FK506, FK520, or rapamycin.

Illustrative of this situation, one can modify the groups at position 9 or 10 of FK506 or FK520 (see Van Duyne et al (1991) Science 252, 839), so as to increase their steric requirement, by replacing the hydroxyl with a group having greater steric requirements, or by modifying the carbonyl at position 10, replacing the carbonyl with a group having greater steric requirements or functionalizing the carbonyl, e.g. forming an N-substituted Schiffs base or imine, to enhance the bulk at that position. Various functionalities which can be conveniently introduced at those sites are alkyl groups to form ethers, acylamido groups, N-alkylated amines, where a 2-hydroxyethylimine can also form a 1,3-oxazoline, or the like. Generally, the substituents will be from about 1 to 6, usually 1 to 4, and more usually 1 to 3 carbon atoms; with from 1 to 3, usually 1 to 2 heteroatoms, which will usually be oxygen, sulfur, nitrogen, or the like. By using different derivatives of the basic structure, one can create different ligands with different conformational requirements for binding. By mutagenizing FK506 ligand binding domains, such as from FKBP12, one can have create a library of potential binding domains which will have different affinities for these modified forms of FK506 or FK520.

For instances, Substituents at C9 and C10 of FK506, which can be and have been accessed by synthesis, clash with a distinct set of FKBP12 sidechain residues. Thus, one class of mutant receptors for such ligands should contain distinct modifications, one creating a compensatory hole for the C10 substituent and one for the C9 substituent. As described in U.S. patent application Ser. No. 08/388,653 by Crabtree et al., carbon 10 was selectively modified to have either an N-acetyl or N-formyl group projecting from the carbon (vs. a hydroxyl group in FK506). The binding properties of these derivatives clearly reveal that these C10 bumps effectively abrogate binding to the native FKBP12. U.S. patent application Ser. No. 08/388,653 by Crabtree et al. depicts schemes for the synthesis of FK506-type moieties containing additional C9 bumps.

This invention thus encompasses use of a class of FK-506-type compounds comprising an FK-506-type moiety which contains, at one or both of C9 and C10, a functional group comprising —OR, —R, —(CO)OR, —NH(CO)H or —NH(CO)R, where R is substituted or unsubstituted, alkyl or arylalkyl which may be straightchain, branched or cyclic, including substituted or unsubstituted peroxides, and carbonates. "FK506-type moieties" include FK506, FK520 and synthetic or naturally occurring variants, analogs and derivatives thereof (including rapamycin) which retain at least the (substituted or unsubstituted) C2 through C15 portion of the ring structure of FK-506 and are capable of binding with a natural or modified FKBP, preferably with a $K_d$ value below about $10^{-6}$M.

Another preferred modified ligand includes FK506 molecules having an addition "bump" at the C9 position of FK506, generating 9-S-methoxy-FK 506 that does not bind endogenous FKBP, but does bind to FKBP12F36V.

To accomodate a substituent at positions 9 or 10 of FK506 or FK520, one can modify FKBP12's Phe36 to Ala and/or Asp37 to Gly or Ala. In particular, mutant FKBP12 moieties which contain Val, Ala, Gly, Met or other small amino acids in place of one or more of Tyr26, Phe36, Asp37, Tyr82 and Phe99 are of particular interest as receptor domains for FK506-type and FK-520-type ligands containing modifications at C9 and/or C10.

Site-directed mutagenesis may be conducted using the megaprimer mutagenesis protocol (see e.g., Sakar and Sommer, *BioTechniques* 8 4 (1990): 404–407). cDNA sequencing is performed with the Sequenase kit. Expression of mutant FKBP12s may be carried out in the plasmid pHN1+ in the *E. coli* strain XA90 since many FKBP12 mutants have been expressed in this system efficiently. Mutant proteins may be conveniently purified by fractionation over DE52 anion exchange resin followed by size exclusion on Sepharose as described elsewhere. See e.g. Aldape et al, *J Biol Chem* 267 23 (1992): 16029–32 and Park et al, *J Biol Chem* 267 5 (1992): 3316–3324. Binding constants may be readily determined by one of two methods. If the mutant FKBPs maintain sufficient rotamase activity, the standard rotamase assay may be utilized. See e.g., Galat et al, *Biochemistry* 31 (1992): 2427–2434. Otherwise, the mutant FKBP12s may be subjected to a binding assay using $LH_2O$ resin and radiolabeled T2-dihydroFK506 and T2-dihyroCsA that we have used previously with FKBPs and cyclophilins. Bierer et al, *Proc. Natl. Acad. Sci. U.S.A.* 87 4 (1993): 555–69.

The invention further provides modified cyclosporin A that cannot bind to its cellular receptor cyclophilin (CypA). As described in the Examples, this rationally modified cyclosporin A is called alpha-cyclopentyl, sarcosine11-CsA (CpSar11-CsA). In addition, the inventors designed and synthesized a cellular receptor cyclophilin (Cyp) with compensatory mutations in its cyclosporin A binding pocket that can form tight complexes with CpSar11-CsA. The rationally designed CpSar11-CsA and its genetically engineered Cyp receptor provide a method to inhibit calcineurin conditionally and tissue specifically through selective expression of this modified cyclophilin receptor.

In another embodiment, modified CsA derivatives for use in the subject invention are CsA analogs in which (a) NMeVal11 is replaced with NMePhe (which may be substituted or unsubstituted) or NMeThr (which may be unsubstituted or substituted on the threonine betahydroxyl group) or (b) the pro-S methyl group of NMeVal11 is replaced with a bulky group of at least 2 carbon atoms, preferably three or more, which may be straight, branched and/or contain a cyclic moiety, and may be alkyl (ethyl, or preferably propyl, butyl, including t-butyl, and so forth), aryl, or arylalkyl. These compounds include those CsA analogs which contain NMeLeu, NMeIle, NMePhe or specifically the unnatural NMe[betaMePhe], in place of MeVal11. The "(b)" CsA compounds are of formula 2 where R represents a functional group as discussed above.

A two step strategy may be used to prepare the modified [MeVal$^{11}$]CsA derivatives starting from CsA. In the first step the residue MeVal11 is removed from the macrocycle. In the second step a selected amino acid is introduced at the (former) MeVal11 site and the linear peptide is cyclized. The synthesis of this compound is further described, e.g., in U.S. application Ser. No. 08/388,653. Mutant cyclophilins that bind such CsA variants by accomodating the extra bulk on the ligand can be prepared and identified, e.g., through the structure-based site-directed and random mutagenesis/ screening protocols, e.g., as described in the FK1012 studies.

Similar considerations apply to the generation of mutant FRAP-derived domains which bind preferentially to rapamycin analogs (rapalogs) containing modifications (i.e., are 'bumped') relative to rapamycin in the FRAP-binding effector domain. For example, one may obtain preferential binding using rapalogs bearing substituents other than —OMe at the C7 position with FRBs based on the human FRAP FRB peptide sequence but bearing amino acid substitutions for one of more of the residues Tyr2038, Phe2039, Thr2098, Gln2099, Trp2101 and Asp2102. Exemplary mutations include Y2038H, Y2038L, Y2038V, Y2038A, F2039H, F2039L, F2039A, F2039V, D2102A, T2098A, T2098N, and T2098S. Rapalogs bearing substituents other than —OH at C28 and/or substituents other than =0 at C30 may be used to obtain preferential binding to FRAP proteins bearing an amino acid substitution for Glu2032. Exemplary mutations include E2032A and E2032S. Proteins comprising an FRB containing one or more amino acid replacements at the foregoing positions, libraries of proteins or peptides randomized at those positions (i.e., containing various substituted amino acids at those residues), libraries randomizing the entire protein domain, or combinations of these sets of mutants are made using the procedures described above to identify mutant FRAPs that bind preferentially to bumped rapalogs.

Further guidance for identifying compensatory mutations to macrolide-binding domains are provided below:

Selection of Compensatory Mutations in FKBP12 for Bump-FK506s Using the Yeast Two-Hybrid System One approach to obtaining variants of receptor proteins or domains, including of FKBP12, is the powerful yeast "two-hybrid" or "interaction trap" system. The two-hybrid system has been used to detect proteins that interact with each other. A "bait" fusion protein consisting of a target protein fused to a transcriptional activation domain is co-expressed with a cDNA library of potential "hooks" fused to a DNA-binding domain. A protein—protein (bait-hook) interaction is detected by the appearance of a reporter gene product whose synthesis requires the joining of the DNA-binding and activation domains. The yeast two-hybrid system mentioned here was originally developed by Elledge and coworkers. Durfee et al, Genes & Development 7 4 (1993): 555–69 and Harper et al, Cell 75 4 (1993): 805–816.

Since the two-hybrid system per se cannot provide insights into receptor-ligand interactions involving small molecule, organic ligands, we have developed a new, FK1012-inducible transcriptional activation system (discussed below). Using that system one may extend the two hybrid system so that small molecules (e.g., FK506s or FK1012s or FK506-type molecules of this invention) can be investigated. One first generates a cDNA library of mutant FKBPs (the hooks) with mutations that are regionally localized to sites that surround C9 and C10 of FK506. For the bait, two different strategies may be pursued. The first uses the ability of FK506 to bind to FKBP12 and create a composite surface that binds to calcineurin. The sequence-specific transcriptional activator is thus comprised of: DNA-binding domain-mutant FKBP 12—bump-FK506—calcineurin A-activation domain (where—refers to a noncovalent binding interaction). The second strategy uses the ability of FK1012s to bind two FKBPs simultaneously.

A HED version of an FK1012 may be used to screen for the following ensemble: DNA-binding domain-mutant FKBP12—bump-FK506-normal FK506—wildtype FKBP12-activation domain.

1. Calcineurin-Gal4 activation domain fusion as a bait: A derivative of pSE1107 that contains the Gal4 activation domain and calcineurin A subunit fusion construct has been constructed. Its ability to act as a bait in the proposed manner has been verified by studies using the two-hybrid system to map out calcineurin's FKBP-FK506 binding site.
2. hFKBP12-Gal4 activation domain fusion as a bait: hFKBP12 cDNA may be excised as an EcoRI-HindIII fragment that covers the entire open reading frame, blunt-ended and ligated to the blunt-ended Xho I site of pSE1107 to generate the full-length hFKBP-Gal4 activation domain protein fusion.
3. Mutant hFKBP12 cDNA libraries hFKBP12 may be digested with EcoRI and HindIII, blunted and cloned into pAS1 (Durfee et al, supra) that has been cut with NcoI and blunted. This plasmid is further digested with NdeI to eliminate the NdeI fragment between the NdeI site in the polylinker sequence of pAS1 and the 5' end of hFKBP12 and religated. This generated the hFKBP12-Gal4 DNA binding domain protein fusion. hFKBP was reamplified. Mutant hFKBP12 cDNA fragments were then prepared using the primers listed below that contain randomized mutant sequences of hFKBP at defined positions by the polymerase chain reaction, and were inserted into the Gal4 DNA binding domain-hFKBP(NdeI/BamHI) construct.
4. Yeast strain S. cerevisiae Y153 carries two selectable marker genes (his3/galctosidase) that are integrated into the genome and are driven by Gal4 promoters. (Durfee, supra.)

Using Calcineurin-Gal4 Activation Domain as Bait

The FKBP12-FK506 complex binds with high affinity to calcineurin, a type 2B protein phosphatase. Since we use C9- or C10-bumped ligands to serve as a bridge in the two-hybrid system, only those FKBPs from the cDNA library that contain a compensatory mutation generate a transcriptional activator. For convenience, one may prepare at least three distinct libraries (using primers 11207–11209, Primer Table) that will each contain 8,000 mutant FKBP12s. Randomized sites were chosen by inspecting the FKBP12-FK506 structure, which suggested clusters of residues whose mutation might allow binding of the offending C9 or C10 substituents on bumped FK506s. The libraries are then individually screened using both C9- and C10-bumped FK506s. The interaction between a bumped-FK506 and a compensatory hFKBP12 mutant can be detected by the ability of host yeast to grow on his drop-out medium and by the expression of -galactosidase gene. Since this selection is dependent on the presence of the bumped-FK506, false positives can be eliminated by substractive screening with replica plates that are supplemented with or without the bumped-FK506 ligands.

Using hFKBP12-Gal4 Activation Domain as Bait

Using the calcineurin A-Gal4 activation domain to screen hFKBP12 mutant cDNA libraries is a simple way to identify compensatory mutations on FKBP12. However, mutations that allow bumped-FK506s to bind hFKBP12 may disrupt the interaction between the mutant FKBP12—bumped-FK506 complex and calcineurin. If the initial screening with calcineurin as a bait fails, the wildtype hFKBP12-Gal4 activation domain will instead be used. An FK1012 HED reagent consisting of: native-FK506-bumped-FK 506 (FIG. 16) may be synthesized and used as a hook. The FK506 moiety of the FK1012 can bind the FKBP12-Gal4 activation domain. An interaction between the bumped-FK506 moiety of the FK1012 and a compensatory mutant of FKBP12 will allow host yeast to grow on his drop-out medium and to express-galactosidase. In this way, the selection is based solely on the ability of hFKBP12 mutant to interact with the bumped-FK506. The same substractive screening strategy can be used to eliminate false positives.

In addition to the in vitro binding assays discussed earlier, an in vivo assay may be used to determine the binding affinity of the bumped-FK506s to the compensatory hFKBP12 mutants. In the yeast two-hybrid system, -gal activity is determined by the degree of interaction between the "bait" and the "prey". Thus, the affinity between the bumped-FK506 and the compensatory FKBP12 mutants can be estimated by the corresponding -galactosidase activities produced by host yeasts at different HED (native-FK 506-bumped-FK506) concentrations.

Using the same strategy, additional randomized mutant FKBP12 cDNA libraries may be created in other bump-contact residues with low-affinity compensatory FKBP12 mutants as templates and may be screened similarly.

Phage Display Screening for High-Affinity Compensatory FKBP Mutations

Some high-affinity hFKBP12 mutants for bump-FK506 may contain several combined point mutations at discrete regions of the protein. The size of the library that contains appropriate combined mutations can be too large for the yeast two-hybrid system's capacity (e.g., $>10^8$ mutations). The use of bacteriophage as a vehicle for exposing whole functional proteins should greatly enhance the capability for screening a large numbers of mutations. See e.g. Bass et al, Proteins: Structure, Function & Genetics 8 4 (1990): 309–14; McCafferty et al, Nature 348 6301 (1990): 552–4; and Hoogenboom, Nucl Acids Res 19 15 (1991): 4133–7. If the desired high-affinity compensatory mutants is not be identified with the yeast two-hybrid system, a large number of combined mutations can be created on hFKBP12 with a phage vector as a carrier. The mutant hFKBP 12 fusion phages can be screened with bumped-FK506-Sepharose as an affinity matrix, which can be synthesized in analogy to our original FK506-based affinity matrices. Fretz et al, J Am Chem Soc 113 4 (1991): 1409–1411. Repeated rounds of binding and phage amplification should lead to the identification of high-affinity compensatory mutants.

Illustrative publications providing additional information concerning synthetic techniques and modifications relevant to FK506 and related compounds include: GB 2 244 991 A; EP 0 455 427 A1; WO 91/17754; EP 0 465 426 A1, U.S. Pat. No. 5,023,263, WO 92/00278, and PCT/US93/01617.

IV. Nucleic Acids Encoding Modified Macrolide-binding, proteins

The invention provides nucleic acids encoding the modified macrolide-binding proteins. In general, nucleic acids encoding wild-type forms of the receptors can be obtained according to methods known in the art. For example, a nucleic acid encoding a receptor can be obtained, e.g, by reverse transcription polymerase chain reaction (RT-PCR) amplification of RNA or PCR amplification of DNA using primers hybridizing to the ends of the nucleic acid desired to be amplified according to methods well known in the art. The nucleotide sequence of the nucleic acids encoding receptors can be found in the litterature or in GenBank, which is publicly accessible on the internet. The template RNA for use in the RT-PCR can be obtained from any cell expressing the transcription factor or DNA binding domain or ligand binding domain. Template DNA can be obtained from any cell, even cells which do not express the desired factor. However, when using DNA as a template, it is preferable to avoid including introns in the construct.

The DNA can be amplified from template RNA or DNA from any species including vertebrates, such as mammals. For gene therapy, the receptor is preferably isolated from a species corresponding to the species of the recipient of the receptor. For example, for gene therapy in humans, the receptor is preferably of human origin. RNA and DNA can be extracted from cells according to methods known in the art.

Further manipulation of the wild-type sequence, e.g., to produce the compensatory mutants, can be carried out by standard molecular biology techniques.

In a preferred embodiment, a DNA encoding the modified target protein is operably linked to a promoter or regulatory element having the desired tissue specificity. Various tissue specific promoters and regulatory elements are known in the art and their nucleic acid sequences are publicly available in GenBank, freely accessible on the internet. Examples of tissue-specific promoters which can be used include the albumin promoter (liver-specific; Pinkert et al. (1987) Genes Dev. 1:268–277), lymphoid-specific promoters (Calame and Eaton (1988) Adv. Immunol. 43:235–275), in particular promoters of T cell receptors (Winoto and Baltimore (1989) EMBO J. 8:729–733) and immunoglobulins (Banerji et al. (1983) Cell 33:729–740; Queen and Baltimore (1983) Cell 33:741–748), neuron-specific promoters (e.g., the neurofilament promoter; Byrne and Ruddle (1989) Proc. Natl. Acad. Sci. U.S.A. 86:5473–5477), pancreas-specific promoters (Edlund et al. (1985) Science 230:912–916), and mammary gland-specific promoters (e.g., milk whey promoter; U.S. Pat. No. <=6> 4,873,316 and European Application Publication No. 264,166). Developmentally-regulated promoters are also encompassed, for example the murine box promoters Kessel and Gruss (1990) Science 249:374–379) and the alpha -fetoprotein promoter (Campes and Tilghman (1989) Genes Dev. 3:537–546). Particularly preferred promoters include T cell specific promoters, such as promoters of T cell receptor genes, CD4 promoter (GenBank Accession No. U01066), and MHC class II promoters (e.g., GenBank Accession No. M81180).

Other regulatory elements of interest for practicing the invention include inducible promoters, which can also be tissue specific. For example, certain regulatory elements are responsive to hormones, such as steroid hormones (e.g., glucocorticoid hormone, MMTV promoter), metal ions (e.g., metallothionein promoter), phorbol esters (TRE elements), or calcium ionophores. Yet other inducible promoters include the growth hormone promoter; promoters which would be inducible by the helper virus such as adenovirus early gene promoter inducible by adenovirus E1A protein, or the adenovirus major late promoter; herpesvirus promoter inducible by herpesvirus proteins such as VP16 or 1CP4; promoters inducible by a vaccinia or pox virus RNA polymerases; or bacteriophage promoters such as T7, T3 and SP6, which are inducible by T7, T3, or SP6 RNA polymeras, respectively.

Other systems permitting an inducible expression of the target protein include tetracyclin-responsive promoters include. Tight control of gene expression in eucaryotic cells has been achieved by use of tetracycline-responsive promoters. Such systems include the "off-switch" systems, in which the presence of tetracyclin inhibits expression, or the "reversible" Tet system, in which a mutant of the E. coli TetR is used, such that the presence of tetracyclin induces expression. These systems are disclosed, e.g., in Gossen and Bujard (Proc. Natl. Acad. Sci. U.S.A. (1992) 89:5547) and in U.S. Pat. Nos. 5,464,758; 5,650,298; and 5,589,362 by Bujard et al. Accordingly, a gene encoding a target protein of the invention can be operably linked to an element responsive to the tetracyclin receptor or mutant form thereof, such that expression of a target gene of the invention is either induced or repressed in the presence of tetracyclin, depending on the system used.

In other embodiments, constitutive promoters may be desirable. There are many strong constitutive promoters that will be suitable for use in the invention, including the adenovirus major later promoter, the cytomegalovirus immediate early promoter, the beta actin promoter, or the beta globin promoter. Many others are known in the art.

For expression of a modified target protein in a cell, a nucleic acid encoding the modified target protein which is operably linked to a promoter is preferably inserted into a vector or plasmid, generally referred to herein as "construct". The constructs can be prepared in conventional ways, where the genes and regulatory regions may be isolated, as appropriate, ligated, cloned in an appropriate cloning host, analyzed by restriction or sequencing, or other convenient means. Particularly, using PCR, individual fragments including all or portions of a functional unit may be isolated, where one or more mutations may be introduced using "primer repair", ligation, in vitro mutagensis, etc. as appropriate. The construct(s) once completed and demonstrated to have the appropriate sequences may then be introduced into the host cell by any convenient means. The constructs may be integrated and packaged into non-replicating, defective viral genomes like Adenovirus, Adeno-associated virus (AAV), or Herpes simplex virus (HSV) or others, including retroviral vectors, for infection or transduction into cells. The constructs may include viral sequences for transfection, if desired. Alternatively, the construct may be introduced by fusion, electroporation, biolistics, transfection, lipofection, or the like. The host cells will usually be grown and expanded in culture before introduction of the construct(s), followed by the appropriate treatment for introduction of the construct(s) and integration of the construct(s). The cells will then be expanded and screened by virtue of a marker present in the construct. Various markers which may be used successfully include hprt, neomycin resistance, thymidine kinase, hygromycin resistance, etc.

In some instances, one may have a target site for homologous recombination, where it is desired that a an expression construct for the modified target protein be integrated at a particular locus. For example, it can knock-out an endogenous gene for the target protein and replace it (at the same locus or elswhere) with the gene encoded for by the construct using materials and methods as are known in the art for homologous recombination. Alternatively, instead of providing a gene encoding a modified target protein, one may modify the endogenous gene encoding the wild-type target protein by, e.g., homologous recombination, such that it encodes the modified form of the protein. See, for example, Thomas and Capecchi, Cell (1987) 51, 503–512; Mansour, et al., Nature (1988) 336, 348–352; and Joyner, et al., Nature (1989) 338, 153–156.

Vectors containing useful elements such as bacterial or yeast origins of replication, selectable and/or amplifiable markers, promoter/enhancer elements for expression in procaryotes or eucaryotes, etc. which may be used to prepare stocks of construct DNAs and for carrying out transfections are well known in the art, and many are commercially available.

The expression constructs of the present invention may be provided in any biologically effective carrier, e.g. any formulation or composition capable of effectively transfecting cells ex vivo or in vivo with the expression construct. Efficient DNA transfer methods have been developed for hematopoietic cells (see, for example, Keating et al. (1990) *Exp Hematol* 18:99–102; and Dick et al. (1986) *Trends Genet* 2:165; and U.S. Pat. Nos. 5,654,185, 5,498,537 and 5,399,346). Approaches include insertion of the subject gene in viral vectors including recombinant retroviruses, adenovirus, adeno-associated virus, and herpes simplex virus-1, or eukaryotic plasmids. Viral vectors can be used to transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out. It will be appreciated that because transduction of appropriate target cells represents the critical first step in gene therapy, choice of the particular gene delivery system will depend on such factors as the phenotype, e.g., the degree of commitment the stem cell has undergone, if any. Another factor in the selection of the appropriate transfection formulation is the consideration raised by ex vivo transfection versus in vivo transfection, with the latter requiring consideration of the route of administration, e.g. locally or systemically.

A preferred approach for both ex vivo or in vivo introduction of the subject target protein gene construct into a cell is by use of a viral vector containing the target protein gene. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors are generally understood to be one of the recombinant gene delivery system of choice for the transfer of exogenous genes into stem cells, particularly into humans cells. (see e.g., Hawley R. G., et al (1994) *Gene Therapy* 1: 136–38)). These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses as a gene delivery system, and defective retroviruses are well characterized for use in gene transfer for gene therapy purposes (for a review, see Miller, A. D. (1990) *Blood* 76:271). Thus, recombinant retrovirus can be constructed in which part of the retroviral coding sequence (gag, pol, env) has been replaced by the target protein gene, rendering the retrovirus replication defective. The replication defective retrovirus is then packaged into virions which can be used to infect a target cell through the use of a helper virus by standard techniques. Protocols for producing recombinant retroviruses and for infecting cells ex vivo or in vivo with such viruses can be found in Ausubel et al., supra, Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include YCrip, YCre, Y2 and YAm.

Retroviruses have been used to introduce a variety of genes into many different cell types, including embryonic stem cells, bone marrow cells, lymphocytes, hepatocytes, and neuronal cells by both ex vivo and in vivo protocols (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Exemplary retroviral vectors have been described that yield a high titre virus capable of efficiently transducing and expressing genes in undifferentiated embryonic and hematopoietic cells (Hawley et al (1994) *Gene Therapy* 1: 136–38). These vectors contain a selectable marker (neo, hph or pac) under the transcriptional control of an internal murine pgk promoter and unique restriction sites for insertion of genes downstream of a variant LTR from the retroviral mutant PCMV (PCC4 embryonal carcinoma cell-passaged myeloproliferative sarcoma virus). A variant of the above-described retroviral vectors, the Murine Stem Cell Virus (MSCV), is illustrated in the examples set out below.

In an exemplary embodiment, the target protein gene is inserted in to the MSCVneo vector (Hawley et al, supra) under the control of the viral LTR promoter and also carrying the neomycin phosphotransferase gene as a selectable marker to confer resistance to G418. Helper-free MSCVneo-target protein virus producing packaging cells (Markowitz et al. (1988) *J Virol* 62:1120–1124) can be made by infection of tunicamycin-treated cells with supernatant from transient transfectants according to the methods of Hawley et al. (1991) *Leukemia Res* 15:659–673. The cells are maintained in, e.g., Dulbecco's modified Eagle medium (DMEM) supplemented with G418. Helper-free MSCVneo-target protein viral stocks can be produced by pooling populations of packaging cells with high titre (e.g., $>10^6$ CFU/ml). The retroviral infection may be performed by either including into the culture medium, supernatants (e.g., 5 to 20% vol/vol) produced by the pooled retroviral packaging cell lines, or by culturing the stem cells directly over the infected retroviral packaging lines themselves, or by both. See, for example, U.S. Pat. Nos. 5,399,493 and 5,399,346 and PCT publication WO 93/07281.

Returning to the general discussion of retroviral vectors, it is noted that the art demonstrates that it is possible to limit the infective spectrum of retroviruses, and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for stem cell surface antigens to the viral env protein (Roux et al. (1989) *PNAS* 86:9079–9083; Julan et al. (1992) *J. Gen Virol* 73:3251–3255; and Goud et al. (1983) *Virology* 163:251–254); or coupling cell surface ligands to the viral env proteins (Neda et al. (1991) *J Biol Chem* 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, and can also be used to convert an ecotropic vector in to an amphotropic vector.

To further illustrate, the target protein gene construct can be generated using a retroviral vector which further provides a fusion protein including the viral envelope protein and the vesicular stomatitis virus (VSV-G) glycoprotein (Burns et al. (1993) *Proc. Natl. Acad. Sci. USA* 90:8033–37; PCT Patent Application WO 92/14829; and WO 96/09400). Unlike typical amphotropic env proteins, the VSV-G protein is thought to mediate viral infection by fusing with a phospholipid component of cell membranes rather than by recognition of a cell surface protein. Since infection is not dependent on a specific receptor, VSV-G pseudotyped vectors have a broad host range. CD34+/Thy-1± mobilized peripheral blood cells have previously been demonstrated to be transduced with high efficiency by a VSV-G pseudotyped retroviral vector (see Kerr et al. PCT publication WO 96/09400). Genetic modification of the stem cells with a target protein gene construct can be accomplished at any point during their maintenance by transduction with VSV-G pseudotyped virion containing the expression construct.

Moreover, use of retroviral gene delivery can be further enhanced by the use of tissue- or cell-specific transcriptional regulatory sequences which control expression of the recombinant target protein gene.

Another viral gene delivery system useful in the present invention utilizes adenovirus-derived vectors. It has been reported, for example, that adenoviral vectors can be used to tranduce human CD34+ hematopoietic cells with high efficiencies. See, for example, Watanabe et al. (1996) *Blood* 87 5032; and *Blood Weekly* Feb. 10, 1997. The genome of an adenovirus can be manipulated such that it encodes the modified target protein, but is inactivate in terms of its ability to replicate in a normal lytic viral life cycle (see, for example, Berkner et al. (1988) *BioTechniques* 6:616; Rosenfeld et al. (1991) *Science* 252:431–434; and Rosenfeld et al. (1992) *Cell* 68:143–155). Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses are relatively stable and amenable to purification and concentration, and as above, can be modified so as to affect the spectrum of infectivity with respect to stem cell populations.

Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham (1986) *J. Virol.* 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) *Cell* 16:683; Berkner et al., supra; and Graham et al. in *Methods in Molecular Biology*, E. J. Murray, Ed. (Humane, Clifton, N.J., 1991) vol. 7. pp. 109–127). Expression of the inserted target protein gene can be under control of, for example, the E1A promoter, the major late promoter (MLP) and associated leader sequences, the E3 promoter, or exogenously added promoter sequences.

Yet another viral vector system useful for delivery of the subject target protein genes is the adeno-associated virus (AAV). Adeno-associated viral vectors have been shown to be effective at transducing other genes into pluripotent hematopoietic stem cells in vitro (see PCT Application WO 96/08560). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro and Immunol.* (1992) 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to a recombinant target protein gene into stem cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081, Wondisford et al. (1988) *Mol. Endocrinol.* 2:32–39, Tratschin et al. (1984) *J. Virol.* 51:611–619; and Flotte et al. (1993) *J. Biol. Chem.* 268: 3781–3790).

In addition to viral transfer methods, such as those illustrated above, non-viral methods can also be employed to cause expression of a heterologous target protein gene in transfected stem cells. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the target protein gene construct by the targeted cell. Exemplary gene delivery systems of this type include liposomal derived systems, poly-lysine conjugates, and artificial viral envelopes.

In a representative embodiment, an expression construct including a target protein gene can be entrapped in liposomes bearing positive charges on their surface (e.g., lipofectins) and (optionally) which are tagged with antibodies against cell surface antigens of the targeted cell population (Mizuno et al. (1992) *No Shinkei Geka* 20:547–551; PCT publication WO91/06309; Japanese patent application 1047381; and European patent publication EP-A43075).

In yet another illustrative embodiment, the gene delivery system comprises an antibody or cell surface ligand which is cross-linked with a gene binding agent such as polylysine (see, for example, PCT publications WO93/04701, WO92/22635, WO92/20316, WO92/19749, and WO92/06180). It will also be appreciated that effective delivery of the subject nucleic acid constructs via receptor-mediated endocytosis can be improved using agents which enhance escape of the gene from the endosomal structures. For instance, whole adenovirus or fusogenic peptides of the influenza HA gene product can be used as part of the delivery system to induce efficient disruption of DNA-containing endosomes (Mulligan et al. (1993) *Science* 260-926; Wagner et al. (1992) *PNAS* 89:7934; and Christiano et al. (1993) *PNAS* 90:2122).

For example, the target protein gene construct can be used to transfect hematopoietic stem cells using a soluble polynucleotide carrier comprising a ligand to a stem cell receptor (e.g., steel factor) conjugated to a polycation, e.g. polylysine. To further illustrate, the gene delivery system can be targeted specifically to c-kit-expressing cells, e.g. human hematopoietic progenitor cells. The c-kit protein is a tyrosine kinase receptor for steel factor and is expressed on pluripotential stem cells capable of reconstituting all hematopoietic lineages. Furthermore, c-kit expression is restricted to stem/progenitor cells, and is not expressed on their committed progeny except for expression in mast cells. In an illustrative embodiment, the expression vector for the target protein gene is condensed by electrostatic forces with polylysine (PL) which has been covalently linked to streptavidin and PL which has been covalently linked to adenovirus (in order to achieve endosomal lysis). To the vector-PL conjugate is added a biotinylated steel factor which becomes associated with the vector-PL conjugate through the streptavidin-biotin interaction. Using such constructs, hematopoietic stem cells can be targeted for transfection with the target protein gene construct. See, for example, U.S. Pat. No. 5,166,320, and Schwarzenberger et al., Blood (1996) 87(2): 472). One advantage to the PL-vector construct described above is the ability to carry out transient transfection of stem cell populations, while committed hematopoietic cells will be refractory to the transfection process because of a lack of c-kit. Another advantage to this approach derives from the fact that DNA uptake relies on highly efficient receptor-mediated endocytosis, a physiological pathway for macromolecular uptake not associated with cellular toxicity. However, in other embodiments, the carrier is conjugated with a ligand (or other binding molecule) specific for certain cell lineages, such as T-cells.

The subject target protein gene constructs can be efficiently introduced into stem cells by DNA transfection or by virus-mediated transduction as extensively described above. In vitro culturing systems known in the art for stem cells provide an accessible model for genetic manipulations. Possible method of transduction include, but are not limited to, direct co-culture of cells with viral producer cells (see, e.g., Bregni et al. (1992) Blood 80: 1418–22). Alternatively, supernatants from virally infected cells can be isolated and applied to cultures of cells under conditions appropriate for infection of the stem cells. See e.g., Xu et al. (1994) Exp. Hemat. 22: 223–30; and Hughes et al. (1992). J. Clin. Invest. 89:1817. The resulting transduced cells may then be grown under conditions similar to those for unmodified stem cells, whereby the modified stem cells may be expanded and caused to differentiate.

The invention also encompasses genetically engineered cells containing and/or expressing any of the constructs described herein, particularly a construct encoding a receptor, including prokaryotic and eucaryotic cells and in particular, yeast, worm, insect, mouse or other rodent, and other mammalian cells, including human cells, of various types and lineages, whether frozen or in active growth, whether in culture or in a whole organism containing them. Several examples of such engineered cells are provided in the Examples which follow.

At present it is especially preferred that the cells be mammalian cells, particularly primate, more particularly human, but can be associated with any animal of interest, particularly domesticated animals, such as equine, bovine, murine, ovine, canine, feline, etc. Among these species, various types of cells can be involved, such as hematopoietic, neural, mesenchymal, cutaneous, mucosal, stromal, muscle, spleen, reticuloendothelial, epithelial, endothelial, hepatic, kidney, gastrointestinal, pulmonary, etc. Of particular interest are hematopoietic cells, which include any of the nucleated cells which may be involved with the lymphoid or myelomonocytic lineages. Of particular interest are members of the T- and B-cell lineages, macrophages and monocytes, myoblasts and fibroblasts. Also of particular interest are stem and progenitor cells, such as hematopoietic neural, stromal, muscle, hepatic, pulmonary, gastrointestinal, etc.

The cells can be autologous cells, syngeneic cells, allogenic cells and even in some cases, xenogeneic cells. The cells may be modified by changing the major histocompatibility complex ("MHC") profile, by inactivating $b_2$-microglobulin to prevent the formation of functional Class I MHC molecules, inactivation of Class II molecules, providing for expression of one or more MHC molecules, enhancing or inactivating cytotoxic capabilities by enhancing or inhibiting the expression of genes associated with the cytotoxic activity, or the like.

In some instances specific clones or oligoclonal cells may be of interest, where the cells have a particular specificity, such as T cells and B cells having a specific antigen specificity or homing target site specificity.

Likewise, this invention encompasses any non-human organism containing such genetically engineered cells. To illustrate this aspect of the invention, an example is provided of a mouse containing engineered cells expressing, in a ligand-dependent manner, an introduced target gene linked to a nucleotide sequence recognized by a transcriptional activator of the invention.

IV. Sources of Cells

Those skilled in the art will appreciate that the subject method can be carried out either in in vivo or ex vivo (e.g., in cell culture) embodiments. The in vivo delivery of a hematopoietic gene construct can be carried out using any of a variety of gene therapy techniques. For ex vivo applications, the stem cell to be genetically modified must first be isolated in cell culture. A variety of protocols for isolating embryonic and/or hematopoietic stem cells are well known in the art. Exemplary stem cell cultures for use in the subject method are described below.

A. Isolation of Hematopoietic Stem Cells

Hematopoietic stem cells (HSCs) can be isolated from a mammalian source including, but not limited to, bone marrow (both adult and fetal), mobilized peripheral blood (MPB), umbilical cord blood and/or fetal liver. In a preferred embodiment, the HSCs are obtained from the subject into which the stem cells are to be transplanted after in vitro culturing and transduction of the hematopoietic gene construct.

The source of cells for the present invention can be, in addition to humans, non-human mammals. A variety of protocols are known in the art for isolating both embryonic stem cells and hematopoietic stem cells from non-human animals. See, for example, the Wheeler U.S. Pat. No. 5,523,226 entitled "Transgenic swine compositions and methods" and the Emery et al. PCT publication WO 95/13363 entitled "Hematopoietic Stem Cells From Swine Cord Blood And Uses Thereof". The preferred non-human animals include vertebrates such as rodents, non-human primates, sheep, dog, cow and pigs. The term "non-human mammal" refers to all members of the class Mammalia except humans.

Where the intended use of the resulting hematopoietic cell is for implantation in human patients, the cells derived from transgenic animals can be used as a source for "humanized"

hematopoietic cells, e.g., for xenogenic grafting into human subjects. For example, as described by the Sachs et al. PCT publication WO 96/06165 entitled "Genetically Engineered Swine Cells", the art provides for implantation of swine donor cells which have been engineered to increase desirable interactions between the donor cells and molecules and cells of a recipient, e.g., to promote the engraftment or function of the donor stem cells in the recipient environment. To illustrate, the cells can be engineered to express a human adhesion molecule, e.g., an adhesion molecule involved in engraftment and/or maintenance of hematopoietic cells. Examples of human adhesion molecules include VLA-4, c-kit, LFA-1, CD11a, Mac-1, CR3, CD11b, p150, p95, CD11c, CD49a, LPAM-1, CD49d, CD44, CD38, and CD34. The transgenic cells can also be engineered to minimize unwanted interactions between the donor cells and molecules and cells of the recipient which, e.g., promote the rejection of donor graft cells or which inhibit the function of the donor graft cells. For example, the donors cells can be derived from a transgenic animal expressing one or more human MHC polypeptides.

Bone marrow cells can be obtained from a source of bone marrow, including but not limited to, ilium (e.g. from the hip bone via the iliac crest), tibia, femora, spine, or other bone cavities. Other sources of stem cells include, but are not limited to, embryonic yolk sac, fetal liver, and fetal spleen.

For isolation of bone marrow, an appropriate solution can be used to flush the bone, e.g., a salt solution supplemented with fetal calf serum (FCS) or other naturally occurring factors, in conjunction with an acceptable buffer at low concentration, generally from about 5–25 mM. Convenient buffers include HEPES, phosphate buffers and lactate buffers. Otherwise bone marrow can be aspirated from the bone in accordance with conventional techniques.

Methods for mobilizing stem cells into the peripheral blood are known in the art and generally involve treatment with chemotherapeutic drugs, cytokines (e.g. GM-CSF, G-CSF or IL3), or combinations thereof. Typically, apheresis for total white cells begins when the total white cell count reaches 500–200 cells/1 and the platelet count reaches 50,000/1.

Various techniques can be employed to separate the cells by initially removing lineage committed cells. Monoclonal antibodies are particularly useful for identifying markers associated with particular cell lineages and/or stages of differentiation. The antibodies can be attached to a solid support to allow for crude separation. The separation techniques employed should maximize the retention of viability of the fraction to be collected. Various techniques of different efficacy can be employed to obtain "relatively crude" separations. Such separations are where up to 10%, usually not more than about 5%, preferably not more than about 1%, of the total cells present not having the marker can remain with the cell population to be retained. The particular technique employed will depend upon efficiency of separation, associated cytotoxicity, ease and speed of performance, and necessity for sophisticated equipment and/or technical skill.

The use of separation techniques include, but are not limited to, those based on differences in physical (density gradient centrifugation and counter-flow centrifugal elutriation), cell surface (lectin and antibody affinity), and vital staining properties (mitochondria-binding dye rho123 and DNA-binding dye Hoechst 33342). Procedures for separation can include, but are not limited to, magnetic separation, using antibody-coated magnetic beads, affinity chromatography, cytotoxic agents joined to a monoclonal antibody or used in conjunction with a monoclonal antibody, including, but not limited to, complement and cytotoxins, and "panning" with antibody attached to a solid matrix, e.g., plate, elutriation or any other convenient technique. Techniques providing accurate separation include, but are not limited to, FACS, which can have varying degrees of sophistication, e.g., a plurality of color channels, low angle and obtuse light scattering detecting channels, impedance channels, etc.

A large proportion of the differentiated cells can be removed by initially using a relatively crude separation, where major cell population lineages of the hematopoietic system, such as lymphocytic and myelomonocytic, are removed, as well as minor populations, such as megakaryocytic, mast cells, eosinophils and basophils. Usually, at least about 70 to 90 percent of the hematopoietic cells will be removed. If desired, a prior separation can be employed to remove erythrocytes, by employing Ficoll-Hypaque separation.

The gross separation can be achieved using methods known in the art including, but not limited to, magnetic beads, cytotoxic agents, affinity chromatography or panning. Antibodies which find use include antibodies to lineage specific markers which allow for removal of most, if not all, mature cells, while being absent on stem cells.

Concomitantly or subsequent to a gross separation, which provides for positive selection, a negative selection can be carried out, where antibodies to lineage-specific markers present on dedicated cells are employed. For the most part, these markers include, but are not limited to, CD2З1, CD3–, CD7–, CD8–, CD10–, CD14–, CD15–, CD16–, CD19–, CD20–, CD33– and glycophorin A; preferably including, but not limited to, at least CD2–, CD14–, CD15–, CD16–, CD19– and glycophorin A; and normally including at least CD14– and CD15–. As used herein, Lin refers to a cell population lacking at least one lineage-specific marker. The hematopoietic cell composition substantially depleted of dedicated cells can then be further separated using a marker for Thy-1, whereby a substantially homogeneous stem cell population is achieved. Exemplary of this stem cell population is a population which is CD34+Thy-1+Lin-, which provides an enriched stem cell composition. Other markers that have been reported to subdivide CD34+cells, further enriching for stem cells include, but are not limited to, CD38–, rhodamine lo, c-kit receptor, HLA DR lo/–, CD71, and CD45 RA–. In fetal tissues and umbilical cord, stem cells are highly enriched in the CD34 hiLin- populations as described by Giusto et al. (1993) Blood 84: 421–32.

The purified stem cells have low side scatter and low to medium forward scatter profiles by FACS analysis. Cytospin preparations show the enriched stem cells to have a size between mature lymphoid cells and mature granulocytes. Cells can be selected based on light-scatter properties as well as their expression of various cell surface antigens.

While it is believed that the particular order of separation is not critical to this invention, the order indicated is preferred. Preferably, cells are initially separated by a coarse separation, followed by a fine separation, with positive selection of a marker associated with stem cells and negative selection for markers associated with lineage committed cells.

Compositions highly enriched in stem cells can be achieved in this manner. The desired stem cells are exemplified by a population with the CD34+Thy-1+Lin- phenotype and being able to provide for cell regeneration and development of members of all of the various hematopoietic lineages.

It should be noted that negative selection lineage selection for lineage specific markers provide a greater enrichment in stem cells obtained from bone marrow than from MPB. The majority of CD34 cells that are mobilized into the peripheral blood do not express lineage-specific markers and, therefore, Lin selection does not significantly enrich over CD34 selection in the peripheral blood as it does in bone marrow. Selection for Thy-1+does enrich for stem cells in both mobilized peripheral blood and bone marrow.

Fetal or neonatal blood are also sources for the hematopoietic stem and progenitor cells of the present invention.

Fetal blood can be obtained by any method known in the art. For example, fetal blood can be taken from the fetal circulation at the placental root with the use of a needle guided by ultrasound (Daffos et al., (1985) *Am. J. Obstet Gynecol* 153:655–660; Daffos et al., (1983) *Am. J. Obstet. Gynecol.* 146:985), by placentocentesis (Valenti, C., (1973) *Am. J. Obstet. Gynecol.* 115:851; Cao et al., (1982) *J. Med. Genet.* 19:81), by fetoscopy (Rodeck, C. H., (1984) in *Prenatal Diagnosis*, Rodeck, C. H. and Nicolaides, K. H., eds., Royal College of Obstetricians and Gynaecologists, London), etc.

In a preferred embodiment of the invention, neonatal hematopoietic stem and progenitor cells can be obtained from umbilical cord blood and/or placental blood. The use of cord or placental blood as a source of hematopoietic cells provides numerous advantages. Cord blood can be obtained easily and without trauma to the donor. In contrast, at present, the collection of bone marrow cells is a traumatic experience which is costly in terms of time and money spent for hospitalization. Cord blood cells can be used for autologous transplantation, when and if needed, and the usual hematological and immunological problems associated with the use of allogeneic cells, matched only partially at the major histocompatibility complex or matched fully at the major, but only partially at the minor complexes, are alleviated.

Collections should be made under sterile conditions. Immediately upon collection, the neonatal or fetal blood should be mixed with an anticoagulent. Such an anticoagulent can be any known in the art, including but not limited to CPD (citrate-phosphate-dextrose), ACD (acid citrate-dextrose), Alsever's solution, De Gowin's Solution, Edglugate-Mg, Rous-Turner Solution, other glucose mixtures, heparin, ethyl biscoumacetate, etc. (See Hurn, B. A. L., 1968, Storage of Blood, Academic Press, New York, pp. 26–160).

B. Isolation of Embryonic Stem Cells

The present system is based on the ability of ES cells to differentiate and generate hematopoietic cells in culture and in vivo. Previous studies have demonstrated that ES cells will differentiate in culture and generate multiple hematopoietic lineages. However, in most of these studies, the extent of hematopoietic development has been limited and variable, and the exact kinetics of hematopoietic differentiation has been unpredictable or poorly defined. Utilizing the subject method, hematopoietic stem cells can be generated by ectopic expression of a hematopoietic gene such as LH-2. The advantages of such a system are several-fold. First, one has access to the cells at all stages of differentiation, making it possible to manipulate the system as it develops. Second, an in vitro system based on ES cells will enable one to study the function of a broad spectrum of genes through inactivation by homologous recombination without encountering the problems inherent to an in vivo system; namely, embryonic lethalities.

Embryonic stem cells are generated and maintained using methods well known to the skilled artisan such as those described by Doetschman et al. (1985) *J. Embryol. Exp. Morphol.* 87:27–45). Any line of ES cells can be used, however, the line chosen is typically selected for the ability of the cells to differentiate into embryoid bodies (EB) followed by their commitment into hematopoietic lineages, e.g. erythroid, lymphoid, myeloid. Thus, any ES cell line from human or non-human origin that is believed to have this capability is suitable for use herein. As an example of one mouse strain that is typically used for production of ES cells, is the 129J strain, e.g. cell line CCE utilized in the Examples below. Still another preferred murine cell line is the cell line J1. Other ES cell lines include D3 (American Type Culture Collection, catalog no. CKL 1934) and the WW6 cell line (see Ioffe et al. (1995) *PNAS* 92:7357–7361).

ES cells are cultured using methods well known to the skilled artisan, such as those set forth by Robertson in: Teratocarcinomas and Embryonic Stem Cells: A Practical Approach, E. J. Robertson, ed. IRL Press, Washington, D.C. [1987]); by Bradley et al. (1986) *Current Topics in Devel. Biol.* 20:357–371); and by Hogan et al. (Manipulating the Mouse Embryo: A Laboratory Manual, Cold Spring Harbor Laboratory Press, Cold Spring Harbor, N.Y. [1986]). As an illustration, ES cells can be grown and passaged in vitro with or without feeder layers, e.g., embryonic fibroblasts, in the presence of growth factors selected from steel factor (membrane-associated or soluble forms), leukemia inhibitory factor (LIF) and fibroblast growth factor (FGF). See e.g., U.S. Pat. No. 5,453,357. Growth and differentiation enhancing concentrations of these factors can range from 0.5–500 ng/ml, preferably, 10–20 ng/ml. Differentiation of ES cells into embryoid bodies (EBs) and multiple cell-types, e.g., hematopoietic, endothelial, muscle and neuronal lineages, can be achieved by a number of standard methods known in the art (reviewed in G. Keller, Current Opinion: 862–69; see also, G. Keller et al. *MCB* 13(1) 473–86).

The technique most frequently used to differentiate ES cells is simply to remove the cells from contact with the feeder cells, or from the presence of LIF, and culture them in liquid or methyl cellulose containing media in bacterial grade petri dishes. Under these conditions, ES cells are unable to adhere to the surface of the dish, and the formation of EBs is enhanced. A modification of this method to maximize ES cell differentiation into hematopoietic lineages involves the culturing of these cells on stromal cells, which provides a supportive environment for hematopoietic cells as they develop within the EBs. Stromal cell culturing methods are extensively described below in *Expansion and Differentiation of Genetically Modified Cells*. Once EBs are formed, they can be dissociated into a single cell suspension. The generated EBs can be assayed at various stages of development for the presence of specific cell populations. For example, hematopoietic lineages can be examined by plating EB-derived cells in methyl cellulose in the presence of growth factors for determining hematopoietic precursor populations. A specific illustration of precursor cell assay is provided in the Examples below. In brief, single cell suspension of EBs can be assayed for precursor content in colony forming cell-culture (CFC-c) assay as described in Keller et al., supra. This procedure will be hereinafter referred to as the precursor assays. Alternatively, EB-derived cells can be analyzed for the presence of specific cell-surface antigens (e.g., immunoglobulin can be used to stain B lymphocytes) by immunocytochemical methods or by FACS analysis. The most stringent test for the differentiation potential of these cells involves the ability of dissociated EB cells to repopulate the hematopoietic system of a recipient animal. Detection of cell surface antigens and transplantation protocols are extensively described below in the section entitled "Expansion and Differentiation of Genetically Modified Cells".

V. Methods of the invention

The invention provides methods for inducing a specific biological activity in a tissue specific manner. In a preferred embodiment, the invention provides a method for modulating cell growth, differentiation and/or survival. According to the method of the invention, a cell is modified to express a modified form of a target protein which mediates the desired biological activity, said target protein interacting specifically with a modified form of a ligand of the target protein, which essentially does not interact with the wildtype target protein.

In a preferred embodiment of the invention, the target protein is a protein involved in the Ca2+/calcineurin pathway, which is involved, in particular in activation of lymphocytes, e.g., T lymphocytes. In an even more preferred embodiment, the target protein is a protein which forms a ternary complex with calcineurin or FRB. Even more preferably, the target protein is cyclophilin, FKBP12, or FRB. Calcineurin is present in most tissues, with the highest level of expression being present in the brain. In lymphocytes, in particular in T cell, calcineurin is involved in activation of the T cells in the presence of Ca2+. Thus, the invention provides a method for regulating T cell activation, e.g., inducing tolerance, without significantly affecting biological activities mediated by calcineurin in other cell types. For example, a population of cells can be engineered to express a modified cyclophilin selectively in T cells, such as by operably linking the gene encoding the modified cyclophilin molecule to a promoter that activates transcription specifically in T cells, e.g, CD4 promoter only the T cells will express the modified cyclophilin and therefore be responsive to the modified ligand. Thus, upon contact with the modified ligand, activation of the T cells expressing the modified cyclophilin will be inhibited, without inducing toxic effects in the cells which do not express the modified cyclophilin.

Furthermore, it has been observed that a reduction in calcineurin activity by only 50% significantly impairs signaling by the antigen receptor on T cells. Similarly, patients treated for transplant rejection have only a 50% reduction in calcineurin activity at the therapeutic concentration of the drug, though they do not usually reject the transplant. In addition, cyclosporin appears to induce tolerance to transplanted tissue even after the drug is withdrawn. For example, in the case of bone marrow populated largely by the transplanted cells, while the lymphocyte population is derived largely or in part from the recipient. Thus, this indicates that blockage of calcineurin action by only 50% for long periods of time results in the development of tolerance to transplanted tissue. Parallel studies in mice have also suggested that these drugs are capable of inducing long term tolerance of transplanted tissues.

Accordingly, the invention is useful in any situation in which tolerance of T lymphocytes is desired. The invention can be applied in vitro or in vivo. In a preferred embodiment, the method is used on cells, e.g, cells obtained from a subject, the cells are modified in vitro and then administered to the subject. In another embodiment, the cells are modified in vivo to express a modified target protein. Conditions which can be treated according to the method of the invention include those involving an immune reaction and are further described below.

In one embodiment, this invention is directed to a method for preventing graft rejection or for treating host versus graft disease following blood marrow transplantation. In one embodiment, the invention, comprises the following steps: (a) inserting DNA encoding a modified cellular target protein, e.g, cyclophilin specific for a modified cyclosporin into a hematopoietic stem cell to produce a transformed hematopoietic stem cell; (b) introducing the transformed hematopoietic stem cell into a recipient mammal, such that the modified cellular target protein cyclophilin is expressed; and, (c) administering an effective amount of the modified cyclosporin to the recipient mammal. As used herein, the term "hematopoietic stem cell" refers to a cell that is capable of developing into mature myeloid and/or lymphoid cells. The method of this invention avoids the undesirable side effect of broad spectrum immune suppressants which are often used in transplantation. The genetic engineering techniques for cloning a protein, transfecting a cell, and introducing the transfected cell into a patient in gene therapy are known. One of skill in this art can determine through routine experimentation the preferred cloning techniques, transfection methods and gene delivery protocol to be used.

In a preferred embodiment, this invention is directed to the modified cyclosporin drug, CpSar11-CsA, which can be administered to the patient receiving the transformed hematopoietic stem cells that are capable of expressing the modified cellular target protein cyclophilin CypAgtm and directed to the modified target protein cyclophilin with the alterations in its amino acid sequence making it specific for the modified cyclosporin CpSar11-CsA.

In another embodiment, the invention is used for treating autoimmune disorders by inducing tolerance of autoimmune cells. Immunosuppressive drugs remain the cornerstone of therapy for autoimmune disorders, although their efficacy is limited and their chronic use entails considerable risk. Immunosuppressive treatment is particularly indicated for progressive neurologic disability without remission when the patient is on a rapidly progressive course. The invention provides a method for treating autoimmune diseases without incurring such risks and toxic effects.

The method according to this invention includes (a) inserting DNA encoding a modified cellular target protein, for example a modified cyclophilin target protein, specific for a modified ligand, cyclosporin, into a T cell to produce a transformed T cell; (b) introducing the transformed T cell into a patient suffering from an autoimmune disorder, such that the modified target protein is expressed, and then, (c) administering to the patient an effective amount of a modified immune agent whose target protein is the modified target protein. In this type of application, specific populations of T cells are transfected and regulated by the modified drug, for example, cyclosporin A. It is preferable that a significant amount of cells are transformed. This can be achieved, by viral transformation, as further described herein. Alternatively, cells can be targeted and transformed in vivo with a construct encoding the modified target protein.

One exemplary autoimmune disease which can be treated according to the method of the invention is multiple sclerosis. Multiple sclerosis (MS) is characterized by chronic inflammation, demyelination, and gliosis (scarring). MS affects 350,000 Americans and is, with the exception of trauma, the most frequent cause of neurologic disability in early to middle adulthood. Indirect evidence supports an autoimmune etiology for MS, perhaps triggered by a viral infection in a genetically susceptible host.

T cells reactive against myelin proteins, either myelin basic protein (MBP) or myelin proteolipid protein (PLP), mediate CNS inflammation in experimental allergic encephalomyelitis (EAE), a laboratory model for demyelinating diseases. This has been proven by adoptive transfer experiments in which sensitized T cells from an animal with EAE can transfer disease to a healthy syngeneic recipient.

It is possible that tissue damage in MS is mediated by cytokine products of activated T cells, macrophages, or astrocytes.

According to this invention, one method of treating MS, particularly in those patients where MS has become life-threatening, is to administer a genetically engineered T cell that expresses a modified target protein for a modified immune agent, such as cyclosporin, FK506, and rapamycin and then administering the modified immunosuppressive drug.

Another exemplary autoimmune disease which can be treated according to the method of the invention is Systemic Lupus Erythematosus (SLE). SLE is a disease of unknown cause in which tissues and cells are damaged by pathogenic autoantibodies and immune complexes. In the United States, the prevalence of SLE in urban areas varies from 15 to 50 per 100,00 population.

SLE probably results from interactions between susceptibility genes and the environment. This interaction results in abnormal immune responses with T and B lymphocyte hyperactivity which is not suppressed by the usual immunoregulatory circuits.

Life threatening, severely disabling manifestations of SLE that are responsive to immunosuppression can be treated according to this invention by administering a genetically engineered T cell that expresses a modified target protein for a modified immune agent and then administering the modified immunosuppressive drug, such as cyclosporin, FK506, or rapamycin.

In addition to autoimmune diseases and graft versus host disease, undesired T cell activation may give rise to a variety of other diseases or conditions, e.g., allograft rejection, hypersensitivity, delayed-type hypersensitivity mediated conditions, and allergic reactions, e.g. drug allergies. Yet other diseases or disorders that can be treated according to the method of the invention include asthma, allergic diseases that have manifestations of inflammations such as dermatitis or rhinitis, for example, atopic dermatitis, symptoms such as bronchoconstriction accompanied by asthma, allergic diseases, rheumatoid arthritis, rheumatoid spondylitis, osteoarthritis, other arthritic conditions, septic shock, septis, and endotoxic shock, atrophic gastritis, thyroiditis, allergic encephalomyelitis, gastric mucosa, thyrotoxicosis, autoimmune hemolytic anemia, thyroidosis, scleroderma, diabetes mellitus, Graves' disease, and sympathetic ophthalmia (Eisen, H. N., 1979, Immunology, Harper and Row, Hagerstown, Md., pp. 557–595).

Another application according to this invention is the selective activation of pathways in cells through receptor-ligand interactions. Thus, a therapeutic protein of choice can be selectively modified to bind with its mutant receptor, which will not bind with other unmodified receptors of "wild-type" or "normal" type, and thus activate the pathway.

For example, the following proteins have known structures and may be modified according to this invention to selectively activate a mutant target protein: human insulin, used in treating diabetes mellitus; human growth hormone, used in treating growth hormone deficiency in children; interferon-alpha, used to treat hairy cell leukaemia and chronic hepatitus A and C; tissue-type plasminogen activator (tPA), used to treat myocardial infarction; erythropoietin, used to treat anaemia in chromic renal failure; granulocyte colony-stimulating factor (G-CSF), used to treat neutropenia following cancer chemotherapy; granulocyte-macrophage colony-stimulating factor (GM-CSF), used for myeloid reconstitution after bone marrow transplantation; and, Factor VIII used in treating haemophilia A.

In another embodiment, the invention can be used to treat neurologic diseases or conditions. For example, in certain conditions, e.g., degenerative diseases, it is desirable to regenerate neurons or other cells of the nervous system, e.g, by implantation of such cells. According to the method of the invention, the growth and/or differentiation of such cells could be controlled, by genetically engineering the cells to express a modified target protein involved in growth, differentiation of cell death control. Methods of genetically modifying donor cells by gene transfer for grafting into the central nervous system to treat defective, diseased or damaged cells are disclosed in U.S. Pat. No. 5,650,148 by Gage et al. The modified donor cells produce functional molecules that effect the recovery or improved function of cells in the CNS. Methods and vectors for carrying out gene transfer and grafting are also described in U.S. Pat. No. 5,650,148.

Alternatively, this invention can be used to engineer ligand-inducable cell death characteristics into cells. Such engineered cells can then be eliminated from a cell culture after they have served their intended purposed (e.g. production of a desired protein or other product) by adding the ligand to the medium. Engineered cells of this invention can also be used in vivo, to modify whole organisms, preferably animals, including humans, e.g. such that the cells produce a desired protein or other result within the animal containing such cells. Such uses include gene therapy.

In one embodiment of the invention, cells are modified ex vivo and introduced into a subject. Depending upon the nature of the cells, the cells may be introduced into a host organism, e.g. a mammal, in a wide variety of ways. Hematopoietic cells may be administered by injection into the vascular system, there being usually at least about $10^4$ cells and generally not more than about $10^{10}$, more usually not more than about $10^8$ cells. The number of cells which are employed will depend upon a number of circumstances, the purpose for the introduction, the lifetime of the cells, the protocol to be used, for example, the number of administrations, the ability of the cells to multiply, the stability of the therapeutic agent, the physiologic need for the therapeutic agent, and the like. Alternatively, with skin cells which may be used as a graft, the number of cells would depend upon the size of the layer to be applied to the burn or other lesion. Generally, for myoblasts or fibroblasts, the number of cells will at least about $10^4$ and not more than about $10^8$ and may be applied as a dispersion, generally being injected at or near the site of interest. The cells will usually be in a physiologically-acceptable medium.

Instead of ex vivo modification of the cells, in many situations one may wish to modify cells in vivo. For this purpose, various techniques have been developed for modification of target tissue and cells in vivo. A number of virus vectors have been developed, such as adenovirus and retroviruses, which allow for transfection and random integration of the virus into the host. See, for example, Dubensky et al. (1984) Proc. Natl. Acad. Sci. USA 81, 7529–7533; Kaneda et al., (1989) Science 243, 375–378; Hiebert et al. (1989) Proc. Natl. Acad. Sci. USA 86, 3594–3598; Hatzoglu et al. (1990) J. Biol. Chem. 265, 17285–17293 and Ferry, et al. (1991) Proc. Natl. Acad. Sci. USA 88, 8377–8381. The vector may be administered by injection, e.g. intravascularly or intramuscularly, inhalation, or other parenteral mode.

In accordance with in vivo genetic modification, the manner of the modification will depend on the nature of the tissue, the efficiency of cellular modification required, the number of opportunities to modify the particular cells, the accessibility of the tissue to the DNA composition to be introduced, and the like. By employing an attenuated or modified retrovirus carrying a target transcriptional initiation region, if desired, one can activate the virus using one of the subject transcription factor constructs, so that the virus may be produced and transfect adjacent cells.

The DNA introduction need not result in integration in every case. In some situations, transient maintenance of the DNA introduced may be sufficient. In this way, one could have a short term effect, where cells could be introduced into the host and then turned on after a predetermined time, for example, after the cells have been able to home to a particular site.

Tissue specific expression of the modified target protein of the invention can also be achieved by selectively introducing a vector encoding the modified target protein in the desired cell type. This can be achieved by various methods. For example, one can choose a viral vector which specifically infects the desired cell type. Alternatively, one can use liposomes, bacteria, or other form of delivery vehicle that can be targeted to the desired cell type by linking to the delivery vehicle a ligand that interacts specifically with the desired cell. The ligand can be a protein, e.g., a growth factor, which interacts with a growth factor target protein on the target cells. In a preferred embodiment, the ligand is altered such that it does not induce a biological activity, but only serves as a target molecule for the construct of the invention. The ligand can be an antibody, specifically recognizing an epitope on the desired target cell. Numerous antibodies to surface molecules are available commercially. Alternatively, antibody molecules can also be prepared according to methods known in the art.

The modified ligand providing for activation of the modified target protein may be administered as desired. Depending upon the binding affinity of the modified ligand, the response desired, the manner of administration, the half-life, the number of cells present, various protocols may be employed. The modified ligand may be administered parenterally or orally. The number of administrations will depend upon the factors described above. The modified ligand may be taken orally as a pill, powder, or dispersion; bucally; sublingually; injected intravascularly, intraperitoneally, subcutaneously; by inhalation, or the like. The modified ligand (and monomeric compound) may be formulated using convenitonal methods and materials well known in the art for the various routes of administration. The precise dose and particular method of administration will depend upon the above factors and be determined by the attending physician or human or animal healthcare provider. For the most part, the manner of administration will be determined empirically.

The particular dosage of the modified ligand for any application may be determined in accordance with the procedures used for therapeutic dosage monitoring, where maintenance of a particular level of expression is desired over an extended period of times for example, greater than about two weeks, or where there is repetitive therapy, with individual or repeated doses of ligand over short periods of time, with extended intervals, for example, two weeks or more. A dose of the modified ligand within a predetermined range would be given and monitored for response, so as to obtain a time-expression level relationship, as well as observing therapeutic response. Depending on the levels observed during the time period and the therapeutic response, one could provide a larger or smaller dose the next time, following the response. This process would be iteratively repeated until one obtained a dosage within the therapeutic range. Where the modified ligand is chronically administered, once the maintenance dosage of the ligand is determined, one could then do assays at extended intervals to be assured that the cellular system is providing the appropriate response and level of the expression product.

It should be appreciated that the system is subject to many variables, such as the cellular response to the ligand, the efficiency of expression and, as appropriate, the level of secretion, the activity of the expression product, the particular need of the patient, which may vary with time and circumstances, the rate of loss of the cellular activity as a result of loss of cells or expression activity of individual cells, and the like. Therefore, it is expected that for each individual patient, even if there were universal cells which could be administered to the population at large, each patient would be monitored for the proper dosage for the individual.

The subject methodology and compositions may be used for the treatment of a wide variety of conditions and indications. For example, B- and T-cells may be used in the treatment of cancer, infectious diseases, metabolic deficiencies, cardiovascular disease, hereditary coagulation deficiencies, autoimmune diseases, joint degenerative diseases, e.g. arthritis, pulmonary disease, kidney disease, endocrine abnormalities, etc. Various cells involved with structure, such as fibroblasts and myoblasts, may be used in the treatment of genetic deficiencies, such as connective tissue deficiencies, arthritis, hepatic disease, etc.

VI. Kits

This invention further provides kits useful for the foregoing applications. One such kit contains one or more nucleic acids encoding a modified target protein thereof. The kit preferably also contains a modified ligand for the target protein. Thus, in one embodiment, the kit comprises a vector containing a gene encoding a modified cyclophilin molecule operably linked to a promoter expressed specifically in T cells and a modified cyclophilin molecule.

The contents of all cited references including literature references, issued patents, published patent applications and co-pending patent applications, as cited throughout this application are hereby expressly incorporated by reference.

EXAMPLES

Example 1

Synthesis of a modified Cyclosporin A, CpSar11-CsA

This Example describes the synthesis of a modified form of Cyclosporin A, termed CpSar11-CsA, which does not significantly interact with the wild-type receptor of cyclosporin A, cyclophilin.

As shown below in Scheme 1, the synthesis of CpSar11-CsA first required the asymmetric synthesis of alpha-cyclopentyl sarcosine using a combination of the methods of Evans, et al. (*J. Am. Chem. Soc.* 112: 4011–4030 (1990)) and Dorow, et al. (*J. Org. Chem.* 60: 4986–7 (1995)) and the subsequent incorporation of this unnatural amino acid into the CsA macrocycle.

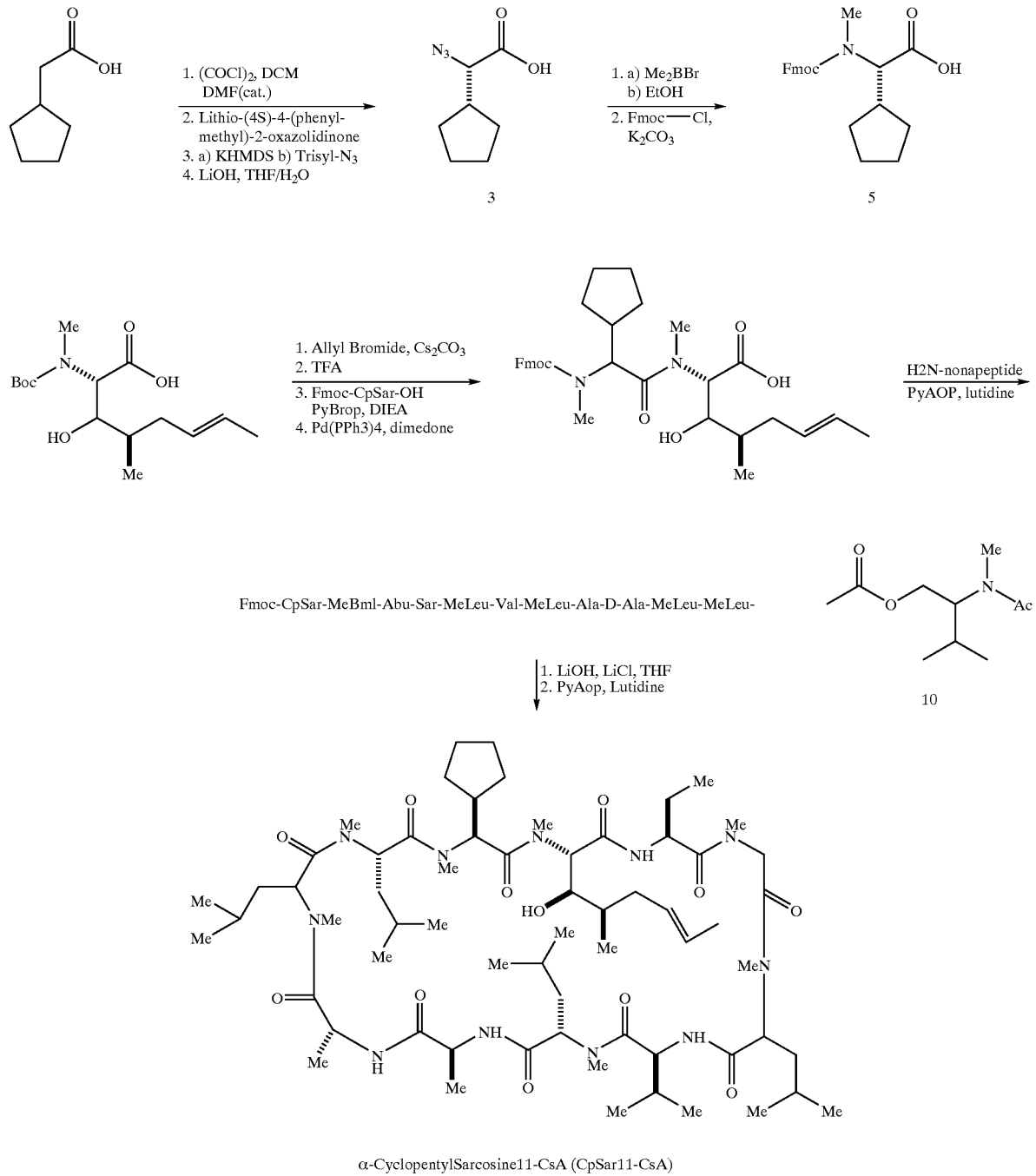

α-CyclopentylSarcosine11-CsA (CpSar11-CsA)

In the synthesis, HZN-nonapeptied (H₂N-Abu-Sar-MeLeu-Val-MeLeu-Ala-DAlaMeleu-MeLeu-(Ac-N-MeValinol ester)), SEQ ID NO: 1, was synthesized from CsA. The reagent abbreviations include the following: DCM, dichloromethane; DMF, dimethylformamide; KHMDS, potassium hexamethyldisilazide; Trisyl-N₃, triisopropylbenzenesulfonylazide; THF, tetrahydrofuran; Fmoc-CL, 9-fluorenylmethylchloroformate; Boc, t-butyloxycarbonyl; TFA, trifluoroacetic acid; PyBrop, bromo-trispyrrolidinophosphonium hexafluorophosphate; DIEA, diisopropylethylamine; dimedone, 5,5-dimethyl-1,4-cyclohexanedione; PyAop, 7-azabenzotriazo-1-yl-oxy(trispyrollidino)phosphonium hexafluorophosphate.

The details of the synthesis are set forth below.

N-α-cyclopentylacetyl-4S-benzyloxazolidinone (1)

To a solution of cyclopentylacetic acid (4.94 g, 38.51 mmol) and DMF (one drop) in DCM (100 mL), oxalylchloride (23.1 mL, 2.0 M in DCM, 1.2 eq, 46.2 mmol) was added dropwise over one hour at room temperature. The reaction was stirred for another two hours, evaporated under reduced pressure and dried under vacuum to afford crude cyclopentylacetyl chloride. This residue was dissolved in THF (80 mL) and cooled to −78° C. To a solution of 4S-benzyloxazolidinone (6.79 g, 38.5 mmol) in THF (50 mL) at −78° C., nBuLi (26.2 mL, 1.45 M, 38 mmol) was added dropwise by syringe and stirred for an additional 15 minutes producing lithiated oxazolidinone. This solution was added over 30 minutes via cannula to the solution of cyclopentylacetyl chloride. The reaction mixture was stirred 30 minutes at −78° C. before quenching with 1 M NaH$_2$SO$_4$ (75 mL). The THF was removed under reduced pressure and the aqueous layer was extracted with DCM (3×75 mL). The combined organics were washed with 10% NaHCO$_3$ aq. (50 mL), brine (50 mL), dried over Na$_2$SO$_4$, filtered and evaporated onto silica (15 g). The product was purified by chromatography (silica gel, 5–20% EtOAc in hexanes) to give 7.97 g (70%) of a white solid: $[\alpha]^{20}$D=+52.00 (c 1, CHCL$_3$); IR (film) 2948, 2835, 1779, 1696, 1455, 1383, 1352, 1210, 1099, 700 cm$^{-1}$; $^1$H NMR (400 MHz, CDCL$_3$) δ 7.2–7.4 (m, 5H), 4.67 (m, 1H), 4.16, (M, 2H), 3.30 (dd, J=3.3, 13.3, 1H), 3.02 (dd, J=6.9, 16.6, 1H), 2.90 (dd, J=7.4, 16.6, 1H), 2.77 (dd, J=9.7, 13.3, 1H), 2.33 (m, 1H), 1.89 (m. 2H), 1.62 (m, 4H), 1.22 (m, 2H); $^{13}$C NMR (100 MHz, CDCL$_3$) δ 172.9, 153.4, 135.3, 127.2, 66.0, 55.1, 41.3, 37.9, 35.7, 32.44, 32.38, 24.9; HRMS (CI+, NH$_3$) calc'd for C$_{17}$H$_{21}$NO$_3$: 305.1865, found 305.1870.

2S-α-azido-α-cyclopentylacetyl-4S-oxalolidinone (2)

To THF (40 mL) at −78° C., potassium hexamethyldisilazide (16.6 mL, 0.91 M in toluene, 1.1 eq. 15.1 mmol) was added and stirred for 10 minutes. A pre-cooled (−78° C.) solution of N-α-cyclopentylacetyl-4S-benzyloxazolidinone 1 (3.94 g, 13.7 mmol) in THF (40 mL) was added and stirred for 30 minutes and followed by a pre-cooled (−78° C.) solution of Trisyl azide (5.09 g, 16.45 mmol, 1.2 eq) in THF (40 mL). After 5 minutes the reaction was quenched with glacial acetic acid (3.65 mL) and warmed to room temperature. The mixture was evaporated to ~20 mL under reduced pressure, diluted with brine (300 mL) and extracted with DCM (3×300 mL). The combined organics were washed with 10% NaHCO$_3$ aq, dried over MgSO4, filtered, evaporated and purified by chromatography (silica gel, 60–100% DCM in hexanes) to give 3.81 g (80%) of a clear oil: $[\alpha]^{20}$D+84.0° (c 1, CDCL$_3$); IR (film) 2957, 2870, 2105, 1781, 1701, 1455, 1387, 1211, 1109, 702 cm$^{-1}$; $^1$H NMR (400 MHz, CDCl$_3$) δ 7.2–7.4 (m, 5H), 4.99 (d, J=8.7, 1H), 4.70 (m, 1H), 4.24, (M, 2H), 3.32 (dd, J=3.3, 13.6, 1H), 2.87 (dd, J=9.4, 13.5, 1H), 2.47 (m, 1H), 1.8–1.9 (m. 1H), 1.5–1.8 (m, 6H), 1.25–1.33 (m, 2H); $^{13}$C NMR (100 MHz, CDCL$_3$) δ 170.4, 152.9, 134.7, 129.4, 127.4, 66.4, 63.2, 55.4, 41.3, 37.5, 29.2, 28.8, 25.3, 25.1 HRMS (CI+, NH$_3$) calc'd for C$_{17}$H$_{20}$N$_4$O$_3$: 346.1879, found 346.1879.

2S-azido-α-cyclopentylacetic acid (3)

To an ice cold solution of the oxazolidinone 2 (3.74 g, 11.4 mmol) in THF/H$_2$O (3/1, 120 mL) was added solid LiOH.H$_2$O (0.955 g, 22.8 mmol, 2 eq). After stirring for 1 hour at 0° C., NaHCO$_3$ aq. (0.5 M, 120 mL) was added and the THF was evaporated under reduced pressure. The aqueous mixture was washed with DCM (4×100 mL), acidified to pH 2 with 3M HCl and extracted with EtOAc (3×150 mL). The combined EtOAc layers were dried over Na$_2$SO$_4$, filtered and evaporated to give 1.85 g (87%) of a clear oil: $[\alpha]^{20}$D=−38.4° (c 0.5, CDCL$_3$); IR (film) 2300–3500 br, 2953, 2103, 1717, 1233, 646, 631, 619 cm$^{-1}$; $^1$H NMR (400 MHz, CDCl$_3$) δ 10.1 (br s, 1H), 3.73 (d, J=7.9, 1H), 2.39 (m, 1H), 1.74–1.9 (m, 2H), 1.54–1.73 (m, 4H), 1.4–1.5 (m, 2H); $^{13}$C NMR (100 MHz, CDCl$_3$) δ 176.5, 65.7, 41.3, 29.3, 28.8, 25.3, 25.1; HRMS (CI+, NH$_3$) calc'd for C$_7$H$_{11}$N$_3$O$_2$: 187.1195, found 187.1189.

L-α-cyclopentylsarcosine (4)

To a solution of the azide 3 (1.29 g, 7.6 mmol) in 1,2-dichloroethane (20 mL) at room temperature was added a solution of bromodimethylborane (1.34 g, 11.1 mmol, 1.46 eq. in 35 mL 1,2 dichloroethane) dropwise over 1.5 hours. After stirring for 1 hour the reaction, EtOH (652 μL, 11.1 mmol, 1.46 eq.) was added, stirred for an additional 20 minutes and concentrated to ~20 mL under reduced pressure. This suspension was triturated with DCM (100 mL) and filtered to give 1.66 g (92%) of an off white solid after drying under vacuum: $[\alpha]^{20}$D=+20.3° (c 1, MeOH); IR (film) 2300–3250 br, 2955, 2350, 1736, 1557, 1460, 1208 cm$^{-1}$; $^1$H NMR (400 MHz, CD$_3$OD) δ 3.93 (d, J=6.4, 1H), 2.74 (s, 3H), 2.38 (m, 1H), 1.75 1.93 (m, 2H), 1.53–1.73 (m, 5H), 1.39–1.5 (m, 1H); $^{13}$C NMR (100 MHz, CD$_3$OD) δ 170.6, 66.1, 41.6, 33.2, 30.2, 29.2, 26, 25.9; HRMS (CI+, NH$_3$) calc'd for C$_8$H$_{15}$NO$_2$: 158.1181, found 158.1185.

9-fluorenylmethyloxycarbonyl-L-α-cyclopentylsarcosine (Fmoc-CpSar-OH) (5)

To a solution of the aminoacid 4 (184 mg, 773 μmol) in H$_2$O/dioxane (1/1, 20 mL), solid Na$_2$CO$_3$ (287 mg, 2.7 mmol, 3.5 eq) and 9-fluorenylmethylchloroformate (300 mg, 1.16 mmol, 1.5 eq.) were added. After stirring overnight at room temperature, more Na$_2$CO$_3$ (100 mg) was added and the reaction was complete after stirring for 1 hour. The reaction mixture was diluted with H$_2$O (30 mL), extracted with EtOAc (2×30 mL), acidified to pH 2 with 3M HCl and extracted with EtOAc (3×30 mL). The combined organics were washed with brine (30 mL), dried over Na$_2$SO$_4$, filtered and evaporated to give 190 mg (95%) of a white solid: $[a]^{20}$D=−45° (c 1, CDCL$_3$); IR (film) 2250–3400 br, 2953, 1740, 1701, 1451, 1402, 1319, 1138, 758, 741 cm$^{-1}$; $^1$H NMR (400 MHz, CDCl$_3$), 2 rotamers, 8 7.77–7.73 (m, 4H), 7.5–7.65 (m, 4H), 7.24–7.43 (m, 8H), 4.41–4.59 (m, 6H), 4.2–4.3 (m, 2H), 4.11–4.17 (m, 1H), 2.91, 2.89 (2s, 6H), 2.39, 2.23 (2m, 2H), 1.94, 1.83 (2m, 2H), 1.35–1.74 (m, 12H), 1.25, 1.01 (2m, 3H); $^{13}$C NMR (100 MHz, CDCL$_3$), 2 rotamers, δ 176.4, 176.3, 157.3, 156.2, 144.1, 144.0, 143.9, 143.9, 143.8, 141.5, 141.4, 141.4, 127.8, 127.7, 127.1, 125.0, 124.9, 120.0, 120.0, 67.9, 67.6, 63.4, 63.0, 47.4, 39.1, 39.0, 31.2, 31.0, 30.6, 29.8, 29.7, 25.6, 25.5, 24.9, 24.8; HRMS (CI+, NH$_3$) calc'd for C$_{23}$H$_{25}$NO$_4$: 380.1862, found 380.1866.

N-tButyloxycarbonyl-(4R)-4-[(E)-2-butenyl]-4,N-dimethyl-L-threonine allyl ester (Boc-MeBmt-O A11) (6)

To a solution of Boc-MeBmt-OH (97 mg, 322 μ mol) in EtOH/H$_2$O (6/1, 3.5 mL), Cs$_2$CO$_3$ (110 mg, 338 μmol, 1.05 eq) was added, stirred for 30 minutes, evaporated and azeotroped with benzene (3×5 mL). The cesium salt was dissolved in DMF (1 mL) and allyl bromide (33.4 μL, 386 μmol, 1.2 eq) was added via syringe and the reaction was stirred overnight at room temperature. The reaction mixture was separated between H$_2$O and diethyl ether (30 mL each), washed with H$_2$O (30 mL), dried over Na$_2$SO$_4$, filtered, evaporated and purified by chromatography (silica gel, 10–25% EtOAc in hexanes) to give 107 mg (97%) of a clear oil: $[\alpha]^{20}$D+0.70 (c 1, CDCL$_3$); IR (film) 3478 br, 2975, 2934, 1750, 1648, 1482, 1451, 1393, 1368, 1323, 1252, 1152, 968, 934, cm$^{-1}$; $^1$H NMR (400 MHz, CDCl$_3$) δ 5.93 (m, 1H), 5.4–5.53 (m, 2H), 5.35 (d, J=17.2, 1H), 5.25 (d, J=10.4, 1H), 4.5–4.85 (m, 3H), 3.75–4.0 (m, 2H), 2.99, 2.95 (2s, 3H), 2.28–2.46 (m, 1H), 1.88–2.03 (m, 1H), 1.67 (d, J=5.0, 3H), 1.48, 1.45 (2s, 9H), 0.87 (d, J=6.7, 3H); $^{13}$C NMR (100 MHz, CDCl$_3$) δ 170.3, 157.2, 131.7, 129.1, 126.9, 118.3, 80.5, 75.5, 65.7, 63.3, 36.1, 35.8, 28.2, 17.9, 15.6; HRMS (CI+, NH$_3$) calc'd for C$_{18}$H$_{31}$NO$_5$: 342.2280, found 342.2264.

HNMeBmt-OA11 (7)

To a solution of Boc-MeBmt-OA11 6 (76.6 mg, 0.22 mmol) in DCM (1 mL) at 0° C., trifluoroacetic acid (0.5 mL) was added dropwise. After stirring for 2 hours, the reaction was quenched into 10% NaHCO$_3$ aq. (30 mL), diluted with H$_2$O (10 mL) and the pH was adjusted to 9.5 with 1N NaOH. This solution was extracted with EtOAc (4×40 mL) and the combined organics were dried over Na$_2$SO$_4$, filtered and evaporated to give 50.2 mg (90%) of a crude oil.

Fmoc-CpSar-MeBmt-OA11 (8)

To a solution of acid 5 (19 mg, 50 µmol, 0.97 eq) and the crude amine 7 (12.5 mg, 52 µmol) in DCM (300 µl), diisopropylethylamine (30 µL) was added followed by PyBrop (29 mg, 62.2 µmol, 1.2 eq) and the reaction was stirred overnight under nitrogen. The reaction mixture was purified by chromatography (silica, 10–20% EtOAc in hexanes to give 10.5 mg (35%) of an oil: IR (film) ? cm$^{-1}$; $^1$H NMR (400 MHz, CDCl$_3$), multiple rotamers, δ 7.2–7.8 (m, 8H), 5.83–6 (m, 1H), 5.2–5.5 (m, 4H), 4.8–5.0 (m, 1H), 4.53–4.75 (m, 3H), 4.4–4.54 (m, 1H), 4.17–4.27 (m, 1H), 3.85–4.15 (m, 1.5H), 3.80 (d, J=10.8, 0.5H), 3.15, 2.84, 2.67, 2.25 (4s, 6H), 2.57–2.67 (m, 0.5H), 2.26–2.4 (m, 1.5H), 1.73–2 (m, 2H), 1.4–1.7 (m, 7H), 1.15–1.35 (m, 3H), 0.72, 0.81, 0.96 (3d, J=6.8, 3H), 0.5, 0.22 (m, 1H); LRMS (FAB+, NaI) calc'd for C$_{36}$H$_{46}$N$_2$O$_6$: 602, found 603, 625 (M+H, M+Na).

Fmoc-CpSar-MeBmt-OH (9)

Allyl ester 8 (8.5 mg, 14.1 µmol) and 3,3-dimethyl-1,5-cyclohexanedione (13.9 mg, 99 µmol, 5 eq) were dissolved in THF (1 mL). A crystal of tetrakis-triphenylphosphine palladium was added and the reaction was stirred under nitrogen at room temperature for 2 hours. The reaction mixture was evaporated under nitrogen and purified by repeated chromatography (silica gel, 0 to 1% HOAc in 50% EtOAc/Hexanes to 1% HOAc in EtOAc) to give 4.3 mg (54%) of an oil: $^1$H NMR (400 MHz, CDCl$_3$), multiple rotamers, δ 7.27–7.8 (m, 8H), 5.3–5.55 (m, 2H), 3.8–4.9 (m, 6.5H), 3.79 (d, J=10.8, 0.5H), 3.15, 2.84, 2.67, 2.25 (4s, 6H), 2.52.67 (m, 0.5H), 2.25–2.4 (m, 1.5H), 1.35–2 (m, 7.5H), 1–1.35 (m, 6.5H), 0.72, 0.81, 0.96 (3d, J=6.8, 3H); LRMS (FAB+, NaI) calc'd for C$_{33}$H$_{42}$N$_2$O$_6$: 562, found 585 (M+Na).

Fmoc-CpSar-MeBmt-Abu-Sar-MeLeu-Val-MeLeu-Ala-D-Ala-MeLeu-Meleuvalinol ester (10), SEQ ID NO: 2

To a solution of acid 9 (4.2 mg, 7.5 µmol) and amine (from deprotection of 4, chapter 4 part 1) (8.42 mg, µmol, 1.0 eq.) and lutidine (10 µL) in DCM (200 µL), PyAop (5.7 mg, µmol, 1.46 eq) was added and the reaction was stirred overnight under nitrogen. The mixture was purified by chromatography (silica gel, 0–20% acetone in EtOAc) to give 12.0 mg (99%) of an oil: $^1$H NMR (500 MHz, CDCl$_3$) many rotamers, possible mixture of diastereomers, finger-print spectra in appendix 1. LRMS (FAB+, NaI) calc'd for C$_{87}$H$_{140}$N$_{12}$O$_{16}$: 1608, found 1609, 1631 (M+H, M+Na).

HNMe-CpSar-MeBmt-Abu-Sar-MeLeu-Val-MeLeu-Ala-D-Ala-MeLeu-Meleu-OH (11), SEQ ID NO: 3

The protected undecapeptide 10 (12 mg, 7.45 µmol), DBU (12 µL) and LiBr (9 mg) were dissolved in THF/H$_2$O (10/1, 330 µL) and stirred for 6 hours at room temperature. More DBU (12 µL) and LiBr (9 mg) were added and the reaction was stirred overnight. After evaporation of the THF under nitrogen, MeOH (500 µL) and a drop of HOAc were added and the solution was filtered through a LH$_2$O column (6 cm×1 cm). Product containing fractions were evaporated, dissolved in phosphate buffer (pH 7) and extracted with DCM (4×15 mL). The combined organics were dried over Na$_2$SO$_4$, filtered and evaporated to give 5.5 mg (59%) of a glassy solid: LRMS (FAB+) calc'd for C$_{64}$H$_{115}$N$_{11}$O$_{13}$: 1245, found 1246 (M+H).

CpSar11-CsA (12)

A solution of the deprotected peptide 11 (5.5 mg, 4.4 µmol), PyAop (23 mg, 44 µmol, 10 eq) and 2,6-lutidine (23 µl) in DCM (10 mL) was stirred for 48 h at RT. The reaction mixture was evaporated and the residue dissolved in MeCN and purified by reverse phase HPLC (Beckman ODS ultra-sphere 5 µl 10 mm×25 cm, 0.1% TFA/MeCN 50:50->10:90 in 25 min., 70° C.) to afford the pure cyclic peptide (2.8 mg, 52%) as a white solid: R$_f$ 0.3 (EtOAc); [a]$^{20}$D −205° (c 0.1, CHCL$_3$); IR (film) 3050–3580 br, 3320, 2957, 2850, 1636, 1558, 1506, 1456, 1412, 1098 cm$^{-1}$; $^1$H NMR (500 MHz, CDCl$_3$) δ=0.71 (d, J=6.0 Hz, 3H, CH$_3$—C(4$^1$)), 0.80–1.10 (m, 33H, CH$_3$—C(3$^2$), 2CH$_3$—C(4$^4$), 2CH$_3$—C(3$^5$), 2CH$_3$—C(4$^6$), 2CH$_3$—C(4$^9$), 2CH$_3$—C(4$^{10}$)), 1.25 (d, J=6.0 Hz, 3H, CH$_3$—C(2$^8$)), 1.35 (d, J=7.2 Hz, 3H, CH$_3$—C(2$^7$)), 1.10–1.80, 1.90–2.20 (m, 25H, H—C(4$^1$), H—C(5$^1$), 2H—C(3$^2$), 2H—C(3$^4$), H—C(4$^4$), 2H—C(3$^6$), H—C(4$^6$), 2H—C(3$^9$), H—C(4$^9$), 2H—C(3$^{10}$), H—C(4$^{10}$), H—C(3$^{11}$), 4H—C(4$^{11}$), 4H—C(5$^{11}$), 1.62 (m, 3H, H—C(8$^1$)), 2.42 (m, 2H, H—C(5$^1$), H—C (3$^5$)), 2.68 (s, 3H, CH$_3$—N$^{10}$), 2.70 (s, 3H, CH$_3$—N$^{11}$), 3.10 (s, 3H, CH$_3$—N$^4$), 3.11 (s, 3H, CH$_3$—N$^9$), 3.26 (s, 3H, CH$_3$—N$^6$), 3.40 (s, 3H, CH$_3$—N$^3$), 3.52 (s, 3H, CH$_3$—N$^1$), 3.20, 4.72 (d, J= 13.9 Hz, 2H, 2H—C(2$^3$)), 3.80 (m, 1H, H—C(3$^1$)), 4.52 (m, 1H, H—C (2$^7$)), 4.65 (m, 1H, H—C(2$^5$)), 4.82 (m, 1H, H—C(2$^8$)), 4.95–5.1 (m, 3H, H—C(2$^2$), H—C(2$^6$), H—C(2$^{10}$)), 5.17 (d, J=11.2 Hz, 1H, H—C(2$^{11}$)), 5.33 (m, 3H, H—C(6$^1$), H—C (7$^1$), H—C(2$^4$)), 5.47 (d, J= 6.2 Hz, 1H, H—C(2$^1$)), 5.69 (dd, J=4.3, 10.9 Hz, 1H, H—C(2$^9$)), 7.18 (d, J=7.9 Hz, 1H, H—N$^8$), 7.46 (d, J=8.5 Hz, 1H, H—N$^5$), 7.69 (d, J=7.5 Hz, 1H, H—N$^7$), 7.99 (d, J= 9.8 Hz, 1H, H—N$^2$).; LRMS (FAB+) calc'd for C$_{64}$H$_{113}$N$_{11}$O$_{12}$: 1227, found 1228 (M+H).

Example 2

Interaction of a Modified Cyclosporin A with a Modified Cyclophilin Induces Gene Activation Selectively in Cells Expressing the Modified Cyclophilin This Example shows that the modified cyclosporin A, CpSar11-CsA, interacts specifically with a modified cyclophilin, CypAgtm, to induce cyclophilin-dependent gene activation.

A modified cyclophilin having the capability to interact with CpSar11-CsA was designed based on the crystal structure of cyclophilin, CypA, and CsA. The crystal structure of the CypA-CsA complex shows that residue 11 of CsA directly contacts Cyp, binding in a deep hydrophobic pocket in the active site of cyclophilin. (See Pflugl, G., et al, *Nature* 361:91–4 (1993) and Ke, H., et al, *Structure* 2:33–44 (1994).) It was reasoned that the addition of atoms at that site should significantly reduce the binding of CpSar11-CsA to CypA, presumably through steric interaction between the side chain of CpSar11 and CypA. To select possible receptors capable of binding CpSar11-CsA, computer models of complexes were generated between CpSar11-CsA and several CypA mutants. Based on these models, three mutations were selected in residues lining the binding pockets of CypA: one to remove the offending steric interaction (phenylalanine at amino acid position thirteen to glycine (F113G)), and two others (serine at amino acid position 99 to threonine (S99T) and cysteine at amino acid position 115 to methionine (C115M)) that improved the fit between the new receptor and ligand.

To determine CpSar11-CsA's binding characteristics, both the unmodified CypA and the modified CypA (S99T, F113G, C115M) (CypAgtm) was overexpressed in *E. coli* and purified according to standard techniques. The binding constants for CpSar11-CsA for each receptor was determined with a direct fluorescence binding assay according to the procedure described in Belshaw, P. J., Schoepher, J. G., Lui, K.-Q., Morrison, K. L. & Schreiber, S. L., *Angew Chem. Int. Ed. Engl.* 34:2129–32 (1995).

As shown in Table 1, CpSar11-CsA has little affinity for wild type CypA, yet binds CypAgtm with high affinity. Kds were determined using a direct fluorescence binding assay as previously described in Belshaw et al., supra.

TABLE I

Cyclophilin binding constants and NFAT-signaling inhibition for CpSar11-CsA

| Assay | Binding Constant Kd | IC50 in Cellular NFAT-Signalling |
|---|---|---|
| CypA wild type + NFAT-SEAP | >5 M | >400 nM |
| CypAgtm + NFAT-SEAP | 9 nM | 25 nM |

Since it is the composite surface of Cyp-CsA that binds to and thereby inhibits the phosphatase activity of Cn and as the modifications to both the receptor and ligand were expected to be buried in the complex, it was expected that these new receptor-ligand combinations would have the ability to inhibit calcineurin (Cn) and thus NFAT mediated gene activation. This hypothesis was confirmed by using a cellular assay in which NFAT-signaling was measured on a reporter gene, as described below.

CypA and mutants were sub-cloned from pGEX based expression vectors into pBJ5, a eukaryotic expression vector containing an N-terminal FLAG epitope tag. The signaling assay was performed as previously described in Belshaw, P. J., Spencer, D. M., Crabtree, G. R. & Schreiber, S. L., *Chemistry & Biology*, 3:731–8 (1996). Briefly $10^7$ Jurkat cells were electroporated with NFAT-SEAP reporter plasmid (1 µg) alone or in combination with a Cyp expression vector (5 µg). After 20 hours, cells were stimulated in 96 well plates with phorbol ester (PMA)(50 ng/mL) and ionomycin (1 µM), which mimics T cell activation and receptor signaling. Varying concentrations of CpSar11-CsA or of CsA were added to the cultures. Twenty-four hours later, cells were assayed for SEAP activity. The data for each transfection are presented as percent SEAP activity relative to the signal for [CpSar11-CsA]=0. Stimulation of these cells with phorbol ester (PMA) and ionomycin, which mimics the T cell receptor signaling, resulted in activation of NFAT via Cn.

The results of this assay, shown in FIG. 1, indicate that CpSar11-CsA had little or no effect on reporter gene expression at concentrations up to 400 nM in cells expressing either endogenous cyclophilins alone or coexpressing a wild type cyclophilin. Yet, in cells expressing CypAgtm, CpSar11-CsA potently inhibited NFAT signaling as shown in FIG. 1 and in Table 1, above. Results were also obtained with the following modified receptor-ligand pairs: a modified cyclophilin A, CypA (S99T, F 113A), referred to herein as CypAat and the modified cyclosporin A, MeIle11-CsA. In fact, in this NFAT-signaling assay, it was found that although MeIle11-CsA potently inhibited NFAT signaling in cells expressing CypAat, MeIle11-CsA still inhibited NFAT signaling in cells transfected with the NFAT reporter gene alone (data not shown). Presumably this was due to formation of endogenous Cyp-MeIle11-CsA complexes that inhibited Cn. In this assay CsA has an IC50 of 15 nM in cells transfected with NFAT-SEAP alone.

As can be seen from these results, the transfected cells were made conditionally sensitive to a drug, dependent on the expression of a dominant allele of its receptor protein.

Example 3

Other Exemplary Modified Cyclophilins and FK506 Molecules which Mediate Gene Activation by Selective Interaction with Modified Receptors This Example describes additional modified cyclosporin and FK506 molecules which selectively interact with a modified cyclophilin and are capable of inducing NF-AT mediated gene transcription.

Figure 2:
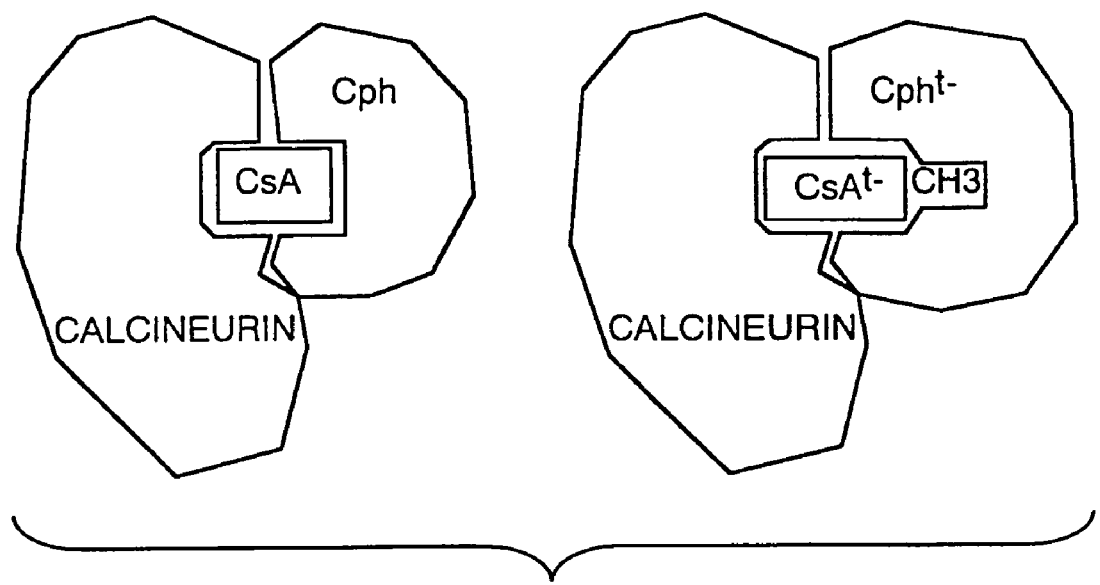
FIG. 2 is a shematic depiction of the interaction between cyclosporin A (CsA) and cyclophilin (Cph) and between a modified CsA (CsAt−), containing an additional methyl group, and a modified Cph (Cpht−) containing mutations of F113G, S99T which create a "hole" to accommodate the methyl group of CsA$^{t-}$.

Altered cyclosporin molecules unable to bind to cyclophilins by virtue of a methyl group at the 11 position of the peptide ring or in another chemical strategy a cyclopentyl sarcosine CsA, were prepared. These molecules, generically referred to as CsA$^{r-}$ after the fact that they are unable to combine with the wild-type cyclophilin to block the activity of calcineurin, are non-toxic and not immunosuppressive in normal cells or whole animals. An engineered cyclophilin molecule binding specifically to these modified cyclosporin and FK506 molecules was prepared. This modified cyclophilin contained mutations of F 113G and S99T, which create a "hole" to accommodate the methyl or pentyl group of CsA$^{r-}$, thus permitting binding to the altered cyclosporins. We call the altered cyclophilins Cph$^{r-}$ since they combine with the non-toxic cyclosporin. A schematic of the binding of the CsA$^{r-}$/Cph$^{r-}$ and the CsA/Cph complexes to the active site of calcineurin is shown in FIG. 2.

In parallel studies altered FK506 molecules were made that have additions "bumps" at the C9 position of FK506 generating 9-S-methoxy-FK506 (FK506$^{r-}$) that does not bind to endogenous FKBP, but does bind to FKBP12F36V (FKBP$^{r-}$).

The affinity of the interaction between cyclosporin and the mutant cyclophilin was measured by binding of labeled protein. These were found to be about 7 nM with no detectable binding to the wildtype Cph. The half time of association and dissociation were similar for the bumped combinations and the wild type combinations. These experiments indicate that the bumped CsA should only be immunosuppressive in cells expressing the compensatory mutant Cph$^{r-}$. In parallel studies the binding of the 9-S-methoxy-FK506 to FKBP12 F36V was found to be 5 nM by Scatchard analysis of the binding of radiolabeled protein to pure FKBP$^{r-}$. On the other hand, FK506 binds to FKBP with a K$_d$ of 0.3 nM in the same assay indicating that some loss of affinity is related to the "bump-hole" combination, which could be optimized by introducing specific mutations and selecting for FKBP molecules having a higher affinity for the bumped FK506.

Figure 3:
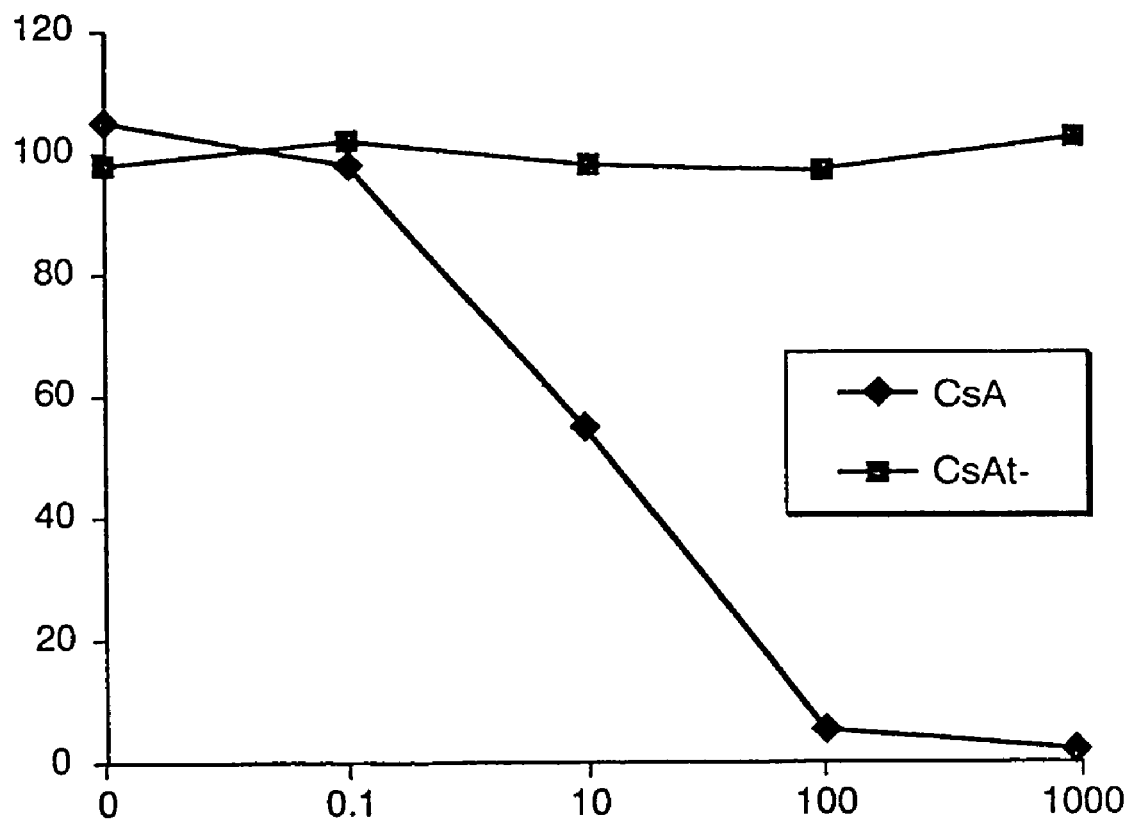
FIG. 3 represents the amount of thymidine incorporated as a percent of maximal stimulation of normal peripheral lymphocytes after 48 hours incubation with anti CD3 plus CD28 and exposure to the indicated concentrations (nM) of CsA or CsA$^{t-}$.

As illustrated in FIG. 3, the bumped cyclosporin does not effect signaling by the antigen receptor. This was shown by incubating human peripheral mononuclear cells from blood donors with anti CD3 and CD28 in the presence of CsA and CsA$^{r-}$ from 0 to 1000 nM. At 48 hours cells were assayed for DNA synthesis by $^3$[H] thymidine incorporation.

Figure 4:
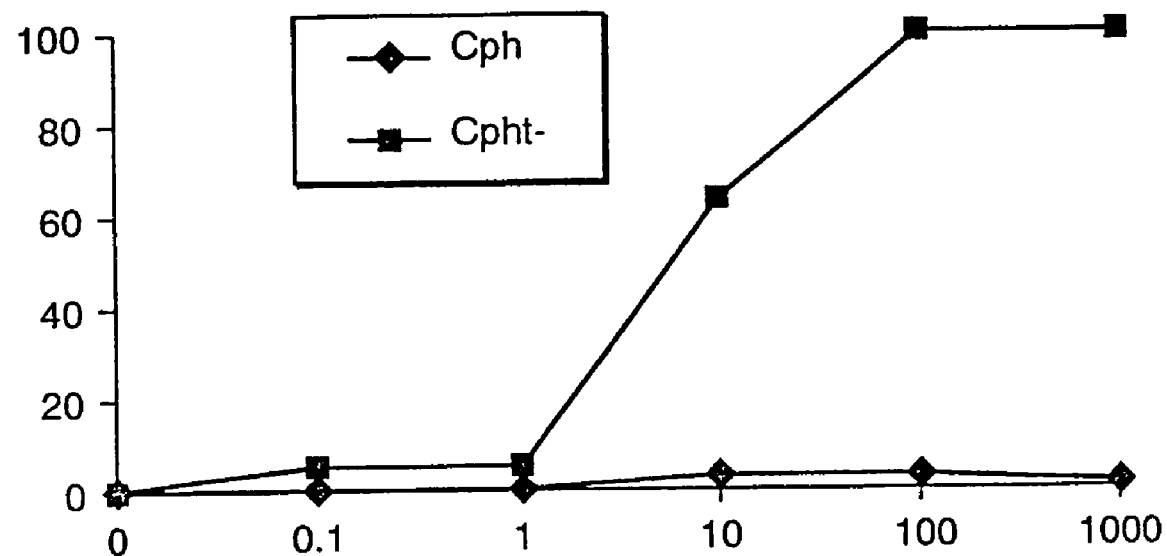
FIG. 4 represents the percent inhibition of NF-AT dependent transcription in Jurkat cells transfected with Cph$^{t-}$or Cph and treated with various concentrations of CsA$^{t-}$.

To determine if the Cph$^{r-}$ would confer selective sensitivity to CsA$^{r-}$ to cells expressing it, Jurkat cells were transfected with the cyclophilin containing the compensatory mutation and tested for NF-AT-dependent transcription. As shown in FIG. 4, CsA$^{t-}$ produced a complete blockage of signaling in cells transfected with Cph$^{t-}$ but not Cph. Similarly, the bumped FK506 (9-methoxy FK506) has no effect on signaling unless cells are transfected with a FKBP containing the compensatory mutation that allows binding of the bumped FK506.

Example 4

Transgenic Mice Sensitive to the Immunosuppressive and Tolerogenic Effects of Cyclosporin A and/or FK506, but Resistant to its Toxic Effects One prediction of the theory that calcineurin is the sole target of the immunosuppressive as well as the toxic side effects of both the cyclosporin A/CpH and FK506/FKBP complexes is that if the formation of these complexes could be directed solely to lymphoid tissue they would be non-toxic for other organs. To do this transgenic mice that express Cpht$^{t-}$ only in T cells and B cells. For expression in T cells, the gene encoding the modified cyclophilin can be operably linked to the CD4 promoter/enhancer. This will result in expression in all T cells from the double positive stage in the thymus to mature peripheral lymphocytes. For expression in B cells, the gene encoding the cyclophilin molecule can be operably linked to the immunoglobulin Eu promoter/enhancer. Both of these promoters have been used frequently in the art to obtain T or B cell specific expression, respectively. The transgenic mice can be prepared according to methods known in the art.

To test the animals for sensitivity to CsA$^{t-}$, peripheral leukocytes can be isolated from these animals and the ability of the transgenic lymphocytes to proliferate in response to irradiated murine fibroblasts from a strain of mouse having an MHC background that gives maximum stimulation with the FYB strain can be tested.

If, as predicted, lymphocyte proliferation is completely inhibited by CsA$^{t-}$, it can be determined if CsA$^{t-}$ can suppress rejection of tissue grafts. This can be done, e.g., by comparing the ability of CsA and CsA$^{t-}$ to block the immune responses to transplanted skin graphs. Groups of 20 mice can be treated with doses of each drug ranging from those required to inhibit 25 to 99% of calcineurin activity assayed by NF-AT dephosphorylation assay using extracts from peripheral blood lymphocytes. This is probably be in the range of 1 mg/kg/day to 10 mg/kg/day. No other immunosuppressive agent should be given and graft rejection can be tested at intervals after initiation of treatment and grafting. Toxic side effects can be assessed by observation for the CNS toxicity which is manifested as ataxia and excessive activity. Renal toxic effects can be assessed by determining the concentration of BUN and creatinine. It is expected that this will show graft survival with fewer toxic side effects.

To test for the ability of CsA$^{t-}$ to prevent the development of self tolerance one can treat the pregnant Cph$^{t-}$ mice with doses of CsA$^{t-}$ that lead to complete suppression of graft rejection and determine if the newborn animals have undergone positive selection as judged by the development of single positive thymocytes and normal numbers of peripheral lymphocytes. Negative selection will be tested by several criteria. The most stringent is the development of autoimmune phenomena after withdrawal of CsA$^{t-}$. If, as predicted, complete suppression of negative selection occurs, it is expected that the animals respond to their own tissue when the signaling pathway is restored by the terminating treatment with the drug. This will be accessed by examination of tissues such as the kidney, pancreas and others for inflammatory infiltrates, by the development of clones of autoreactive T cells judged by the failure of super antigen reactive cells to be deleted, and by the development of auto antibodies to classic self antigens such as DNA, and ribonuclear proteins.

To show that CsA$^{t-}$ can suppress graft rejection, skin grafts from non-compatible mice can be implanted into Cph$^{t-}$ transgenic mice, which can then be treated with CsA$^{t-}$ and rejection of the graft will be assessed using well defined criteria. As previously shown for cyclosporin A, it is expected that CsA$^{t-}$ will suppress rejection. To determine if long term total blockage of the antigen receptor signaling pathway will lead to tolerance to the transplanted tissue the animals can be treated for various lengths of time after transplantation with CsA$^{t-}$. It will then be tested if withdrawal of CsA$^{t-}$ will allow continued suppression of graft rejection implying that the animals were made tolerant to the transplanted tissue.

To show that CsA$^{t-}$ can prevent graft-vs-host disease, bone marrow can be taken from Cph$^{t-}$ mice and transferred to irradiated MHC-mismatched mice and the mice observed for the development of graft-vs-host disease. Animals can be treated with CsA$^{t-}$ for 1, 2, 4, or 8 weeks after transplantation with the dose necessary to inhibit: a) 50% or b) 99% of calcineurin activity in lymphocytes. In other experiment, purified stem cells from the Cph$^{t-}$ mice can be used to do the transplantation.

The transgenic Cph$^{t-}$ mice can also be used to confirm that complete blockage of the calcineurin/NF-AT pathway will prevent the development of autoimmune diabetes in NOD mice.

Cph$^{t-}$ transgenic mice can be made either directly in NOD mice or in the FYB strain to facilitate breeding to the NOD mice as described above. Transgenic mice can be crossed with the NOD mice and followed for the expression of Cph$^{t-}$ at levels approximating those of the endogenous Cph A gene. Once backcrossing is complete, the animals will be tested for the development of diabetes.

To test the effects of CsA$^{t-}$ on the development of diabetes in the NOD mice, these can be administered CsA$^{t-}$ at specific times during fetal life (p.c. day 14 to 21), after birth, 0–3 weeks, 4–8 weeks, 4–12 weeks, and 4–16 weeks. It is expected, based at least in part on previous results obtained, that CsA$^{t-}$ will suppress the development of autoimmune diabetes. Animals will be monitored for the symptoms of diabetes as known in the art and including: 1) determining the presence of auto antibodies to GAD, HSP70, CPH; 2) T cell activation and 3) islet inflammation and lymphoid infiltration.

The transgenic mice can also be used to show that long term suppression of the calcineurin/NF-AT, pathway with CsA$^{t-}$ can lead to tolerance and the prevention of diabetes in the absence of continued CsA$^{t-}$ treatment. The ability of CsA$^{t-}$ to induce long term tolerance and prevention of inflammation in the islets of the NOD mice can be tested by withdrawing CsA$^{t-}$ at various times after the initiation of treatment The times until the development of symptoms will the be measured as defined above. In addition animals can be monitored for the development of auto antibodies to GAD, CPH, and HSP70. If the animals do not develop auto antibodies and do not develop disease after ceasing immunosuppression with CsA$^{t-}$, this will be indicative that the suppression of the $Ca^{2+}$/calcineurin pathway can lead to the development of tolerance and address the question of the underlying mechanism.

Although the foregoing invention has been described in some detail by way of illustration and example for purposes of clarity of understanding, it will be obvious to one skilled in the art that certain changes and modifications may be practiced within the scope of the appended claims.

What is claimed is:

1. A method for inhibiting proliferation of genetically engineered T cells in an animal, wherein said genetically engineered T cells are introduced to the animal and said genetically engineered T cells comprise a nucleic acid encoding a mutated macrolide binding protein (MBP) selected from an FK506-binding protein (FKBP), cyclophilin, calcineurin, and FKBP:rapamycin associated protein (FRAP), wherein said method comprises administering to the animal a macrolide which binds to the mutated MBP or forms a complex including the mutated MBP, thereby inhibiting proliferation of T cells expressing the mutated MBP, wherein said genetically engineered T cells are autologous or allogeneic to the animal, and wherein, relative to the wild-type MBP, the mutated MBP contains an altered amino acid sequence and has an altered specificity for binding to or forming a complex with a macrolide.

2. The method of claim 1, wherein the macrolide binds to or forms a complex with the mutated MBP with a dissociation constant, $K_d$, at least one order of magnitude less than its $K_d$ for binding to or forming a complex with wild-type MBP.

3. The method of claim 1, wherein the macrolide binds to or forms a complex with the mutated MBP with a dissociation constant, $K_d$, at least three orders of magnitude less than its $K_d$ for binding to or forming a complex with wild-type MBP.

4. The method of claim 1, wherein the nucleic acid was introduced into said T cell ex vivo by DNA transfection.

5. The method of claim 1, wherein the nucleic acid was introduced into said T cell ex vivo by virus-mediated transduction.

6. The method of claim 1, wherein the nucleic acid was introduced into said T cell ex vivo by homologous recombination.

7. The method of claim 1, wherein the macrolide is an analog of rapamycin, FK506 or cyclosporin.

8. The method of claim 1, wherein the animal is a mammal.

9. The method of claim 8, wherein the animal is a human.

10. The method of claim 1, wherein the expression of the mutated nucleic acid is transcriptionally regulated by a T-cell specific transcriptional regulatory sequence.

11. A method for providing an animal comprising genetically engineered T cells, wherein the proliferation of said T cells is preferentially inhibited, said method comprising introducing into said animal said genetically engineered T cells, which comprise a nucleic acid encoding a mutated macrolide binding protein (MBP), wherein
   (a) said mutated MBP is selected from an FK506-binding protein (FKBP), cyclophilin, calcineurin, and FKBP: rapamycin associated protein (FRAP); and
   (b) relative to the wild-type MBP, the mutated MBP contains an altered amino acid sequence has an altered specificity for binding to or forming a complex with a macrolide.

* * * * *

UNITED STATES PATENT AND TRADEMARK OFFICE
CERTIFICATE OF CORRECTION

| | |
|---|---|
| PATENT NO. | : 6,982,082 B1 |
| APPLICATION NO. | : 08/922240 |
| DATED | : January 3, 2006 |
| INVENTOR(S) | : Schreiber et al. |

It is certified that error appears in the above-identified patent and that said Letters Patent is hereby corrected as shown below:

In Claim 11, Col. 48, line 71, insert --; (c) wherein said genetically engineered T cells are autolouous or allogeneic to the animal-- after the word macrolide.

Signed and Sealed this

Twenty-second Day of August, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,982,082 B1 | Page 1 of 1 |
| APPLICATION NO. | : 08/922240 | |
| DATED | : January 3, 2006 | |
| INVENTOR(S) | : Schreiber et al. | |

It is certified that error appears in the above-identified patent and that said Letters Patent is hereby corrected as shown below:

In the Specification Under Column 1:

• Please replace Column 1, line no. 7-11 with:

-- FEDERALLY-SPONSORED RESEARCH OR DEVELOPMENT
This invention was made with Government support under contract CA039612 awarded by the National Institutes of Health. The Government has certain rights in this invention. --

Signed and Sealed this
Third Day of April, 2012

David J. Kappos
*Director of the United States Patent and Trademark Office*

SEQUENCE LISTING

<160> NUMBER OF SEQ ID NOS: 3

<210> SEQ ID NO 1
<211> LENGTH: 10
<212> TYPE: PRT
<213> ORGANISM: Unknown
<220> FEATURE:
<223> OTHER INFORMATION: synthetic modified cyclosporin A peptide
<220> FEATURE:
<221> NAME/KEY: VARIANT
<222> LOCATION: 1
<223> OTHER INFORMATION: Xaa = Abu: alpha-aminobutyric acid
<220> FEATURE:
<221> NAME/KEY: VARIANT
<222> LOCATION: 2
<223> OTHER INFORMATION: Xaa = Sar: sarcosine
<220> FEATURE:
<221> NAME/KEY: VARIANT
<222> LOCATION: 3, 5, 8, 9
<223> OTHER INFORMATION: Xaa = MeLeu: N-methylleucine
<220> FEATURE:
<221> NAME/KEY: VARIANT
<222> LOCATION: 7
<223> OTHER INFORMATION: Xaa = D-Ala: D-alanine
<220> FEATURE:
<221> NAME/KEY: VARIANT
<222> LOCATION: 10
<223> OTHER INFORMATION: Xaa = Ac-N-MeValinol ester

<400> SEQUENCE: 1

Xaa Xaa Xaa Val Xaa Ala Xaa Xaa Xaa Xaa
 1               5                  10

<210> SEQ ID NO 2
<211> LENGTH: 12
<212> TYPE: PRT
<213> ORGANISM: Unknown
<220> FEATURE:
<223> OTHER INFORMATION: synthetic modified cyclosporin A peptide
<220> FEATURE:
<221> NAME/KEY: VARIANT
<222> LOCATION: 1
<223> OTHER INFORMATION: Xaa = Fmoc-CpSar:
    9-fluorenylmethoxycarbonyl-cyclopentyl sarcosine
<220> FEATURE:
<221> NAME/KEY: VARIANT
<222> LOCATION: 2
<223> OTHER INFORMATION: Xaa = MeBmt:
    (4R)-N-methyl-4-butenyl-4-methyl-L-threonine
<220> FEATURE:
<221> NAME/KEY: VARIANT
<222> LOCATION: 3
<223> OTHER INFORMATION: Xaa = Abu: alpha-aminobutyric acid
<220> FEATURE:
<221> NAME/KEY: VARIANT
<222> LOCATION: 4
<223> OTHER INFORMATION: Xaa = Sar: sarcosine
<220> FEATURE:
<221> NAME/KEY: VARIANT
<222> LOCATION: 5, 7, 10, 11
<223> OTHER INFORMATION: Xaa = MeLeu: N-methylleucine
<220> FEATURE:
<221> NAME/KEY: VARIANT
<222> LOCATION: (9)...(9)
<223> OTHER INFORMATION: Xaa = D-Ala: D-alanine
<220> FEATURE:
<221> NAME/KEY: VARIANT
<222> LOCATION: (12)...(12)
<223> OTHER INFORMATION: Xaa = Valinol ester

<400> SEQUENCE: 2

Xaa Xaa Xaa Xaa Xaa Val Xaa Ala Xaa Xaa Xaa Xaa
 1               5                  10

```
-continued

<210> SEQ ID NO 3
<211> LENGTH: 11
<212> TYPE: PRT
<213> ORGANISM: Unknown
<220> FEATURE:
<223> OTHER INFORMATION: synthetic modified cyclosporin A peptide
<220> FEATURE:
<221> NAME/KEY: VARIANT
<222> LOCATION: 1
<223> OTHER INFORMATION: Xaa = Me-CpSar: methyl-cyclopentyl sarcosine
<220> FEATURE:
<221> NAME/KEY: VARIANT
<222> LOCATION: 2
<223> OTHER INFORMATION: Xaa = MeBmt:
      (4R)-N-methyl-4-butenyl-4-methyl-L-threonine
<220> FEATURE:
<221> NAME/KEY: VARIANT
<222> LOCATION: 3
<223> OTHER INFORMATION: Xaa = Abu: alpha-aminobutyric acid
<220> FEATURE:
<221> NAME/KEY: VARIANT
<222> LOCATION: 4
<223> OTHER INFORMATION: Xaa = Sar: sarcosine
<220> FEATURE:
<221> NAME/KEY: VARIANT
<222> LOCATION: 5, 7, 10
<223> OTHER INFORMATION: Xaa = MeLeu: N-methylleucine
<220> FEATURE:
<221> NAME/KEY: VARIANT
<222> LOCATION: (9)...(9)
<223> OTHER INFORMATION: Xaa = D-alanine
<220> FEATURE:
<221> NAME/KEY: VARIANT
<222> LOCATION: (11)...(11)
<223> OTHER INFORMATION: Xaa = MeLeu-(OH): hydroxyl-N-methylleucine

<400> SEQUENCE: 3

Xaa Xaa Xaa Xaa Xaa Val Xaa Ala Xaa Xaa Xaa
1               5                   10
```